United States Patent [19]

Smallheer

[11] Patent Number: 5,543,517
[45] Date of Patent: Aug. 6, 1996

[54] SUBSTITUTED BICYCLIC PHOSPHORAMIDES AND DERIVATIVES THEREOF

[75] Inventor: Joanne M. Smallheer, Landenberg, Pa.

[73] Assignee: The DuPont Merck Pharmaceutical Company, Wilmington, Del.

[21] Appl. No.: 181,117

[22] Filed: Jan. 13, 1994

[51] Int. Cl.$^6$ .................. C07D 413/14; A61K 31/33
[52] U.S. Cl. .................. 544/151; 546/22; 544/337; 548/119; 568/12; 558/75; 562/507
[58] Field of Search .................. 568/12; 514/80, 514/81, 96, 100, 111; 544/151, 337; 546/22; 548/119; 564/16; 562/507; 560/125; 558/75

[56] References Cited

U.S. PATENT DOCUMENTS 4,966,895  10/1990  Tolman et al. .................. 514/81

OTHER PUBLICATIONS

Wei et al, Nature, 373(6510), 117–122, (Jan. 1995).
Ho et al, Nature, 373 (6510), 123–126 (Jan. 1995).
Wain–Hobson, Nature, 373(6510), 102 (Jan. 1995).
Tummino et al, Biochemical and Biophysical Research Communications, 201(1), 290–294, (May 1994).
Kempf et al, Proceedings of the National Academy of Sciences, 92(7), 2484–2488, (Mar. 1995).
Islam et al, Journal of Medicinal Chemistry, 37(2), 293–304, (Jan. 1994).
Fehrentz et al, Biochemical and Biophysical Research Communications, 188(2), 873–878, (Oct. 1995).
Kempf et al, Journal of Medicinal Chemistry, 36(3), 320–330, (Feb. 1993).
Huff, Journal of Medicinal Chemistry, 34(8), 2314–2327, (Aug. 1991).
Thaisrivongs et al, Journal of Medicinal Chemistry, 37(20), 3200–3204, (Sep. 1994).
Nifant'ev, N. S., Chemical Abstracts, vol. 116, #235,725, abstract of Zh. Obsch–Khim., 61(11), 2505–13, 1991.
Socol, S. M., et al., Chemical Abstracts, vol. 105, #34,573, abstract of Inorg. Chem., 25(15), 2658–2653, 1986.

*Primary Examiner*—Mukund J. Shah
*Assistant Examiner*—Matthew V. Grumbling

[57] ABSTRACT

This invention relates to substituted bicyclic phosphoramides and derivatives thereof, useful as retroviral protease inhibitors and as standards and reagents in determining the ability of a potential pharmaceutical to inhibit viral replication or HIV protease, to pharmaceutical compositions comprising such compounds, and to methods of using these compounds for treating viral infection.

4 Claims, No Drawings

SUBSTITUTED BICYCLIC PHOSPHORAMIDES AND DERIVATIVES THEREOF

FIELD OF THE INVENTION

This invention relates to substituted bicyclic phosphoramides and derivatives thereof useful as retroviral protease inhibitors, to pharmaceutical compositions comprising such compounds, and to methods of using these compounds for treating viral infection.

BACKGROUND OF THE INVENTION

Current treatments for viral diseases usually involve administration of compounds that inhibit viral DNA synthesis. For example, current treatments for acquired immunodeficiency syndrome (AIDS) include administration of compounds such as 2',3'-dideoxycytidine, trisodium phosphonoformate, ammonium 21-tungsto-9-antimoniate, 1-β-D-ribofuranoxyl-1,2,4-triazole-3-carboxamide, 3'-azido-3'-deoxythymidine (AZT), and adriamycin, all of which inhibit viral DNA synthesis, see, e.g., Dagani, *Chem. Eng. News,* Nov. 23, 1987 pp. 41–49. Alternatively, compounds such as AL-721 or polymannoacetate may be administered to prevent human immunodeficiency virus (HIV) from penetrating the host cell. Also, compounds which treat the opportunistic infections caused by the immunosupression resulting from HIV infection are known. However, none of the current AIDS treatments has proven to be totally effective in treating and/or reversing the disease. In addition, many of the compounds currently used to treat AIDS cause adverse side effects including platelet count, renal toxicity, and bone marrow cytopenia.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. However, no therapeutically useful renin protease inhibitors have been developed, due to problems of oral bioavailability and in vivo stability of candidate inhibitors.

Retrovirus genome encodes a protease that can accomplish the proteolytic processing of one or more polyprotein precursors, such as the polyprotein precursors encoded by the pol and gag genes. See Wellink *Arch. Virol.* 1988, 98, 1. Retroviral proteases most commonly process the polyprotein precursor encoded by the gag gene into its core proteins, and process the polyprotein precursor encoded by the pol gene into the enzymes reverse transcriptase and retroviral protease.

The correct processing of precursor polyproteins by retroviral protease is necessary for assembly of infectious virions. It has been shown that the in vitro mutagenesis that produces a protease-defective virus also leads to the production of immature core forms of the virus which lack infectivity. See Crawford et al. *J. Virol.* 1985, 53, 899 and Katoh et al. *Virology* 1985, 145, 280. Therefore, retroviral protease inhibition provides an attractive target for antiviral therapy, see Mitsuya, *Nature* 1987, 325, 775. The inhibition of viral protease provides a method for blocking viral replication, and therefore a treatment for viral diseases, such as AIDS, that may have fewer side effects, be more efficacious, and be less prone to drug resistance when compared to current treatments.

Moore Biochem. *Biophys. Res. Commun.* 1989, 159, 420 discloses peptidyl inhibitors of HIV protease. Erickson, PCT Patent Application Publication No. WO 89/10752 discloses derivatives of peptides that are inhibitors of HIV protease. U.S. Pat. No. 4,652,552 discloses methyl ketone derivatives of tetrapeptides as inhibitors of viral proteases. U.S. Pat. No. 4,644,055 discloses halomethyl derivatives of peptides as inhibitors of viral proteases. PCT Patent Application Publication No. WO 87/07836 discloses L-glutamic acid gamma-monohydroxamate as an antiviral agent. PCT Patent Application Publication No. WO 93/07128, the disclosure of which is hereby incorporated herein by reference, discloses synthetic procedures for preparing HIV protease inhibitors.

A large number of compounds, e.g., renin, have been reported to be proteases inhibitors. However, many of these compounds suffer from an inability to reach their targets (bioavailability), particularly if oral administration is desired, and thus are not altogether satisfactory therapeutic agents. This poor activity has been variously ascribed to the relatively high molecular weight and size of most protease inhibitors, to solubility properties that work against free transport of the inhibitors, and to vulnerability of the peptide bonds in the inhibitors to in vivo cleavage by mammalian proteases, resulting in the inhibitor and fragments thereof becoming bound to human serum.

The present invention concerns novel substituted bicyclic phosphoramides and derivatives thereof, which are capable of inhibiting viral protease and thereby provide a means of combating virus induced diseases, such as AIDS. The substituted bicyclic phosphoramides of the invention provide significant improvements over protease inhibitors that are known in the art. The substituted bicyclic phosphoramides and derivatives of the present invention afford distinct benefits in overcoming problems of recognized protease inhibitors, in that they do not contain peptide bonds, and can be hydrophilic yet still inhibit viral protease enzyme. The inhibitors of the invention are also of low molecular weight, and therefore can be expected to have good oral absorption properties in mammals.

Additionally, known inhibitors of other non-HIV proteases do not inhibit HIV protease. The structure-activity requirements of such inhibitors differ from those of HIV protease inhibitors. The substituted bicyclic phosphoramides and derivatives thereof of the invention are particularly useful as inhibitors of HIV protease and similar retroviral proteases.

The invention also provides materials useful as standards and reagents in determining the ability of a potential pharmaceutical to inhibit viral replication and/or HIV protease. These would be provided as a commercial kit comprising a compound provided by this invention.

SUMMARY OF THE INVENTION

One aspect of this invention is a compound of formula (I):

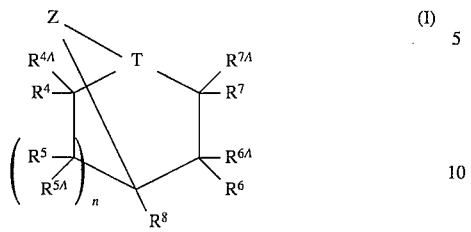

or a pharmaceutically acceptable salt or prodrug form thereof wherein:

Each of $R^4$ and $R^7$ is independently:
hydrogen, —$O(R^{13})$, —$S(R^{13})$, —$C(=O)O(R^{13})$,
$C_1$-$C_8$ alkyl substituted with 0–3 $R^{11}$,
$C_2$-$C_8$ alkenyl substituted with 0–3 $R^{11}$,
$C_2$-$C_8$ alkynyl substituted with 0–3 $R^{11}$,
a $C_3$-$C_{14}$ carbocyclic ring system substituted with 0–3 $R^{11}$ or 0–3 $R^{12}$, or
a 5- to 10-membered heterocyclic ring system containing 1 to 4 heteroatoms independently selected from oxygen, nitrogen or sulfur, the heterocyclic ring system being substituted with 0–2 $R^{12}$;

Each of $R^{4A}$ and $R^{7A}$ is independently:
hydrogen, —$O(R^{13})$, —$S(R^{13})$, —$C(=O)O(R^{13})$,
$C_1$-$C_4$ alkyl unsubstituted or substituted with halogen or $C_1$-$C_2$ alkoxy, or
phenylmethyl unsubstituted or substituted with halogen or $C_1$-$C_2$ alkoxy;

Each of $R^5$ and $R^{5A}$ is independently:
hydrogen, halogen, —$N(R^{20})_2$, —$S(R^{20})$, —$O(R^{20})$ or $C_1$-$C_6$ alkyl substituted with 0–3 $R^{11}$;
$R^5$ and $R^{5A}$ can alternatively join to form =O, =S or a ketal ring;

Each of $R^6$ and $R^{6A}$ is independently:
hydrogen, halogen, —$N(R^{20})_2$, —$S(R^{20})$, —$O(R^{21})$ or $C_1$-$C_6$ alkyl substituted with 0–3 $R^{11}$;
$R^6$ and $R^{6A}$ can alternatively join to form =O, =S or a ketal ring;

$R^8$ is: hydrogen, $C_1$-$C_3$ alkyl or $C_1$-$C_3$ perfluoroalkyl;
$R^8$ can alternatively join with any of $R^5$, $R^{5A}$, $R^6$ or $R^{6A}$ to form —$OCH_2SCH_2O$—, —$OS(=O)O$—, —$OC(=O)O$—, —$OCH_2O$—, —$OC(=S)O$—, —$OC(=O)C(=O)O$—, —$OC(CH_3)_2O$—, —$OC((CH_2)_3NH_2)(CH_3)O$—, —$OC(OCH_3)(CH_2CH_2CH_3)O$—, —$OS(=O)_2O$—, —$NHC(=O)NH$—, —$OC(=O)NH$—, —$NHC(=O)O$—, —$NHCH_2O$—, —$OCH_2NH$—, —$NHC(=S)O$—, —$OC(=S)NH$—, —$OS(=O)NH$—, —$NHS(=O)O$—, —$NHC(=O)C(=O)O$—, —$OC(=O)C(=O)NH$—, —$NHC(=O)C(=O)NH$—, —$NHC(CH_3)_2O$—, —$OC(CH_3)_2NH$— or any group that, when administered to a mammalian subject as part of a compound of formula (I), cleaves to form a compound having two free hydroxyl groups, or two free amino groups, or one free hydroxyl and one free amino group;

Each $R^{11}$ is independently:
hydrogen, keto, halogen, phenylmethyl, phenethyl, methylenedioxy, ethylenedioxy, hydroxamic acid, hydrazide, boronic acid, sulfonamide, azido, formyl, phenoxy, phenylmethoxy, nitro, cyano, —$CH_2N(R^{13})(R^{14})$, —$N(R^{13})(R^{14})$, —$OCH_2C(=O)OH$, —$C(=O)O(R^{13})$, —$OC(=O)(R^{13})$, —$O(R^{13})$, $C_2$-$C_6$ alkoxyalkyl, —$S(=O)_m(R^{13})$, —$NHC(=NH)NH(R^{13})$, —$C(=NH)NH(R^{13})$, —$C(=O)N(R^{13})(R^{14})$, —$N(R^{14})C(=O)(R^{13})$, =N—$O(R^{14})$, —$N(R^{14})C(=O)O(R^{14})$, —$OC(=O)N(R^{13})(R^{14})$, —$N(R^{13})C(=O)N(R^{13})(R^{14})$, —$C(R^{14})=N$—$O(R^{14})$, —$N(R^{14})S(=O)_2N(R^{13})(R^{14})$, —$N(R^{14})S(=O)_2(R^{13})$, —$S(=O)_2N(R^{13})(R^{14})$, $C_1$-$C_4$ alkyl, $C_2$-$C_4$ alkenyl, $C_3$-$C_{10}$ cycloalkyl, $C_3$-$C_6$ cycloalkylmethyl, $C_7$-$C_{10}$ arylalkyl, $C_3$-$C_6$ cycloalkoxy, $C_1$-$C_4$ alkyl substituted with —$N(R^{13})(R^{14})$, $C_1$-$C_4$ hydroxyalkyl, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, 2-(1-morpholino)ethoxy, —($C_1$-$C_3$ alkyl)aryl substituted with 0–2 $R^{12}$,
a $C_5$-$C_{14}$ carbocyclic residue substituted with 0–3 $R^{12}$, or
a 5- to 10-membered heterocyclic ring system containing 1 to 4 heteroatoms independently selected from oxygen, nitrogen or sulfur, the heterocyclic ring system being substituted with 0–3 $R^{12}$;

m is: 0, 1 or 2;
Each $R^{11A}$ is independently:
H, keto, halogen, cyano, —$CH_2NH_2$, —$NH_2$, —$CO_2H$, —$OC(=O)$ ($C_1$-$C_3$ alkyl), —OH, $C_2$-$C_6$ alkoxyalkyl, —$C(=O)NH_2$, —$OC(=O)NH_2$, —$NHC(=O)NH_2$, —$S(=O)_2NH_2$, $C_1$-$C_4$ alkyl, $C_2$-$C_4$ alkenyl, $C_3$-$C_{10}$ cycloalkyl, $C_3$-$C_6$ cycloalkylmethyl, benzyl, phenethyl, phenoxy, benzyloxy, nitro, $C_7$-$C_{10}$ arylalkyl, hydroxamic acid, hydrazide, boronic acid, $C_3$-$C_6$ cycloalkoxy, $C_1$-$C_4$ alkyl substituted with —$NH_2$, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —$OCH_2C(=O)OH$, 2-(1-morpholino)ethoxy, azido, aryl($C_1$-$C_3$ alkyl), a $C_5$-$C_{14}$ carbocyclic residue, or a 5- to 10-membered heterocyclic ring system containing 1 to 4 heteroatoms independently selected from oxygen, nitrogen or sulfur;

Each $R^{12}$ when a substituent on carbon, is independently:
phenyl, phenylmethyl, phenethyl, phenoxy, phenylmethoxy, halogen, hydroxy, nitro, cyano, $C_1$-$C_4$ alkyl, $C_3$-$C_6$ cycloalkyl, $C_3$-$C_6$ cycloalkylmethyl, $C_7$-$C_{10}$ arylalkyl, $C_1$-$C_4$ alkoxy, —$C(=O)OH$, hydroxamic acid, hydrazide, boronic acid, sulfonamide, formyl, $C_3$-$C_6$ cycloalkoxy, —$O(R^{13})$, $C_1$-$C_4$ alkyl substituted with —$N(R^{13})$ $(R^{14})$, —$N(R^{13})$ $(R^{14})$, $C_2$-$C_6$ alkoxyalkyl, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —$S(=O)_m(R^{13})$, —$S(=O)_2N(R^{13})$ $(R^{14})$, —$NHS(=O)_2(R^{14})$, —$OCH_2C(=O)OH$, 2-(1-morpholino)ethoxy, —$C(R^{14})=N$—$O(R^{14})$,
a 5- to 10-membered heterocyclic ring containing from 1 to 4 heteroatoms independently selected from oxygen, nitrogen or sulfur, the heterocyclic ring system being substituted with 0–3 $R^{15}$,
a 3- or 4-carbon chain attached to an adjacent carbon on the ring to which it is appended to form a fused 5- or 6-membered ring, the 5- or 6-membered ring being optionally substituted on any of the aliphatic carbons with halogen, $C_1$-$C_4$ alkyl, $C_1$-$C_4$ alkoxy, hydroxy, —$N(R^{13})$ $(R^{14})$, or
when $R^{12}$ is attached to a saturated carbon atom, $R^{12}$ may be =O or =S;

Each $R^{12}$, when a substituent on nitrogen, is independently:
  phenyl, phenylmethyl, phenethyl, hydroxy, $C_1$-$C_4$ hydroxyalkyl, $C_1$-$C_4$ alkoxy, $C_1$-$C_4$ alkyl, $C_3$-$C_6$ cycloalkyl, $C_3$-$C_6$ cycloalkylmethyl, —$CH_2N(R^{13})$ $(R^{14})$, —$N(R^{13})$ $(R^{14})$, $C_2$-$C_6$ alkoxyalkyl, $C_1$-$C_4$ haloalkyl, $C_1$-$C_4$ alkoxycarbonyl, —C(=O)OH, $C_1$-$C_4$ alkylcarbonyloxy, $C_1$-$C_4$ alkylcarbonyl or —$C(R^{14})$=N—$O(R^{14})$;
Each $R^{13}$ is independently:
  hydrogen, phenyl substituted with 0–3 $R^{11A}$, phenylmethyl substituted with 0–3 $R^{11A}$, $C_1$-$C_6$ alkyl substituted with 0–3 $R^{11A}$, $C_2$-$C_4$ alkenyl substituted with 0–3 $R^{11A}$, $C_1$-$C_6$ alkylcarbonyl substituted with 0–3 $R^{11A}$, $C_1$-$C_6$ alkoxycarbonyl substituted with 0–3 $R^{11A}$, $C_1$-$C_6$ alkylaminocarbonyl substituted with 0–3 $R^{11A}$, $C_3$-$C_6$ alkoxyalkyl substituted with 0–3 $R^{11A}$, an amine protecting group when $R^{13}$ is bonded to N, or a hydroxy protecting group when $R^{13}$ is bonded to O;
Each $R^{14}$ is independently:
  hydrogen, hydroxy, trifluoromethyl, $C_1$-$C_6$ alkoxy, $C_2$-$C_6$ alkenyl, phenylmethyl, amino,
  $C_1$-$C_6$ alkyl substituted with 0–3 groups selected from hydroxy, $C_1$-$C_4$ alkoxy, halogen, amino,
  an amine protecting group when $R^{14}$ is bonded to N, or a hydroxy protecting group when $R^{14}$ is bonded to O;
$R^{13}$ and $R^{14}$ can alternatively join to form: —$(CH_2)_4$—, —$(CH_2)_5$—, —$CH_2CH_2N(R^{15})CH_2CH_2$— or —$CH_2CH_2OCH_2CH_2$—;
$R^{15}$ is: hydrogen or methyl;
Each of $R^{20}$ and $R^{21}$ is independently:
  hydrogen, $C_1$-$C_6$ alkyl substituted with 0–3 $R^{11}$, $C_3$-$C_6$ alkoxyalkyl substituted with 0–3 $R^{11}$, $C_1$-$C_6$ alkylcarbonyl substituted with 0–3 $R^{11}$, $C_1$-$C_6$ alkoxycarbonyl substituted with 0–3 $R^{11}$, $C_1$-$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, or any group that, when administered to a mammalian subject as part of a compound of formula (I), cleaves to form a free hydroxyl, free amino or free sulfhydryl;
T is:
  —$N(R^{22})P(=O)N(R^{23})$—, —$N(R^{22})P(=O)O$—, —$OP(=O)N(R^{23})$—, —$N(R^{22})P(=O)C(R^{27})(CR^{28})$—, —$C(R^{25})$ $(R^{26})P(=O)N(R^{23})$—, —$N(R^{22})P(=O)S$—, —$SP(=O)N(R^{23})$—, —$C(R^{25})(R^{26})P(=O)C(R^{27})$ $(R^{28})$—, —$C(R^{25})(R^{26})P(=O)O$—, —$OP(=O)C(R^{27})$ $(R^{28})$—, —$C(R^{25})(R^{26})P(=O)S$—, —$SP(=O)C(R^{27})$ $(R^{28})$—,
  —$N(R^{22})P(=S)N(R^{23})$—, —$N(R^{22})P(=S)C(R^{27})(CR^{28})$—, —$C(R^{25})$ $(R^{26})P(=S)N(R^{23})$—, —$N(R^{22})P(=S)O$—, —$OP(=S)N(R^{23})$—, —$N(R^{22})P(=S)S$—, —$SP(=S)N(R^{23})$—, —$C(R^{25})(R^{26})P(=S)C(R^{27})$ $(R^{28})$—, —$C(R^{25})(R^{26})P(=S)O$—, —$OP(=S)C(R^{27})$ $(R^{28})$—, —$C(R^{25})(R^{26})P(=S)S$—, —$SP(=S)C(R^{27})$ $(R^{28})$—,
  —$N(R^{22})P(=Se)N(R^{23})$—, —$N(R^{22})P(=Se)C(R^{27})(CR^{28})$—, —$C(R^{25})$ $(R^{26})P(=Se)N(R^{23})$—, —$N(R^{22})P(=Se)O$—, —$OP(=Se)N(R^{23})$—, —$N(R^{22})P(=Se)S$—, —$SP(=Se)N(R^{23})$—, —$C(R^{25})(R^{26})P(=Se)C(R^{27})$ $(R^{28})$—, —$C(R^{25})(R^{26})P(=Se)O$—, —$OP(=Se)C(R^{27})$ $(R^{28})$—, —$C(R^{25})(R^{26})P(=Se)S$— or —$SP(=Se)C(R^{27})$ $(R^{28})$—;
Each of $R^{22}$ and $R^{23}$ is independently:
  hydrogen, $C_1$-$C_8$ alkyl substituted with 0–3 $R^{31}$, $C_2$-$C_8$ alkenyl substituted with 0–3 $R^{31}$, $C_2$-$C_8$ alkynyl substituted with 0–3 $R^{31}$,
  a $C_3$-$C_{14}$ carbocyclic ring system substituted with 0–5 $R^{31}$ or 0–5 $R^{32}$, or
  a 5- to 10-membered heterocyclic ring system containing 1 to 4 heteroatoms independently selected from oxygen, nitrogen or sulfur, the heterocyclic ring system being substituted with 0–2 $R^{32}$;
Z is: O, $N(R^{24A})$ or $C(R^{24A})_2$;
Each $R^{24A}$ is independently:
  hydrogen, $C_1$-$C_6$ alkyl or $C_1$-$C_6$ alkoxy;
Each of $R^{25}$ and $R^{27}$ is independently:
  hydrogen, —$O(R^{13})$, —$S(R^{13})$, $C_1$-$C_8$ alkyl substituted with 0–3 $R^{31}$, $C_2$-$C_8$ alkenyl substituted with 0–3 $R^{31}$, $C_2$-$C_8$ alkynyl substituted with 0–3 $R^{31}$,
  a $C_3$-$C_{14}$ carbocyclic ring system substituted with 0–5 $R^{31}$ or 0–5 $R^{32}$, or
  a 5- to 10-membered heterocyclic ring system containing 1 to 4 heteroatoms independently selected from oxygen, nitrogen or sulfur, the heterocyclic ring system being substituted with 0–2 $R^{32}$;
Each of $R^{26}$ and $R^{28}$ is independently:
  hydrogen, halogen, —$O(R^{13})$, —$S(R^{13})$,
  $C_1$-$C_4$ alkyl substituted with 0–3 halogen or 0–3 $C_1$-$C_2$ alkoxy, or
  phenylmethyl substituted with 0–3 halogen or 0–3 $C_1$-$C_2$ alkoxy;
Each $R^{31}$ is independently:
  keto, halogen, cyano, —$CH_2N(R^{13})$ $(R^{14})$, —$N(R^{13})$ $(R^{14})$, —$C(=O)O(R_{13})$, —$C(=O)$ $(R^{11})$, —$OC(=O)(R^{13})$, —$O(R^{13})$, $C_2$-$C_6$ alkoxyalkyl, —$S(=O)_m(R^{13})$, —$NHC(=NH)NH(R^{13})$, —$C(=NH)NH(R^{13})$, —$C(=O)N(R^{13})$ $(R^{14})$, —$N(R^{14})C(=O)$ $(R^{13})$, =N—$O(R^{14})$, —$N(R^{14})C(=O)O(R^{14})$, —$OC(=O)N(R^{13})$ $(R^{14})$, —$N(R^{13})C(=O)N(R^{13})$ $(R^{14})$, —$N(R^{14})S(=O)_2N(R^{13})$ $(R^{14})$, —$N(R^{14})S(=O)_2(R^{13})$, —$S(=O)_2N(R^{13})$ $(R^{14})$, $C_1$-$C_4$ alkyl, $C_2$-$C_4$ alkenyl, $C_3$-$C_{10}$ cycloalkyl, $C_3$-$C_6$ cycloalkylmethyl, phenylmethyl, phenethyl, phenoxy, phenylmethoxy, nitro, $C_7$-$C_{10}$ arylalkyl, hydroxamic acid, hydrazide, oxime, boronic acid, sulfonamide, formyl, $C_3$-$C_6$ cycloalkoxy, $C_1$-$C_4$ alkyl substituted with —$N(R^{13})$ $(R^{14})$, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —$OCH_2C(=O)O(R^{13})$, 2-(1-morpholino)ethoxy, azido, —$C(R^{14})$=N—$O(R^{14})$,
  a $C_5$-$C_{14}$ carbocyclic residue substituted with 0–5 $R^{32}$,
  or a 5- to 10-membered heterocyclic ring system containing 1 to 4 heteroatoms independently selected from oxygen, nitrogen or sulfur, the heterocyclic ring system being substituted with 0–2 $R^{32}$;
Each $R^{32}$, when a substituent on carbon, is independently:
  phenethyl, phenoxy, $C_3$-$C_{10}$ cycloalkyl, $C_3$-$C_6$ cycloalkylmethyl, $C_7$-$C_{10}$ arylalkyl, hydrazide, oxime, $C_2$-$C_6$ alkoxyalkyl, methylenedioxy, ethylenedioxy, $C_1$-$C_4$ alkylcarbonyloxy, —$NHS(=O)_2(R^{14})$, phenylmethoxy, halogen, 2-(1-morpholino)ethoxy, —$C(=O)O(R^{13})$, hydroxamic acid, —$C(=O)N(R^{13})N(R^{13})$ $(R^{14})$, cyano, boronic acid, sulfonamide, formyl, $C_3$-$C_6$ cycloalkoxy, $C_1$-$C_4$ haloalkyl, $C_1$-$C_4$ haloalkoxy, $C_2$-$C_4$ haloalkenyl, $C_2$-$C_4$ haloalkynyl, —$N(R^{13})$ $(R^{14})$, —$C(R^{14})$=N—$O(R^{14})$, —$NO_2$, —$O(R^{13})$, —$N(R^{40})$ $(R^{41})$, —$S(=O)_m(R^{13})$, —$S(=O)_mN(R^{13})$ $(R^{14})$, —$C(=O)N(R^{13})$ $(R^{14})$, —$OC(=O)N(R^{13})$ $(R^{14})$, —$C(=O)$ $(R^{11})$, —$OC(=O)$ ($R^{11}$), —OC(=O)O($R^{13}$), phenyl, —C(=O)N($R^{13}$)—($C_1$-$C_4$ alkyl)—N($R^{13}$) ($R^{14}$), —C(=O)N($R^{40}$) ($R^{41}$), —C(=O)N($R^{13}$)C($R^{11}$)$_2$N($R^{13}$) ($R^{14}$), —C(=O)N($R^{13}$)C($R^{11}$)$_2$N($R^{13}$)NH($R^{14}$), —C(=O)N($R^{13}$)C($R^{11}$)$_2$N($R^{13}$)C(=O)O($R^{13}$), —C(=O)N($R^{13}$)—($C_1$-$C_4$ alkyl)—N($R^{13}$)C(=O)O($R^{13}$), —C(=O)N($R^{13}$)—($C_1$-$C_4$ alkyl)—$R^{11}$, —C(=O)C($R^{11}$)$_2$N($R^{13}$) ($R^{14}$), —C(=O)C($R^{11}$)$_2$N($R^{13}$)NH($R^{14}$), —C(=O)C($R^{11}$)$_2$N($R^{13}$)C(=O)O($R^{13}$), —C(=O)—($C_1$-$C_4$ alkyl)—N($R^{13}$) ($R^{14}$), —C(=O)—($C_1$-$C_4$ alkyl)—N($R^{13}$)C(=O)O($R^{13}$), $C_1$-$C_4$ alkoxy substituted with 0–4 groups selected from: $R^{11}$, $C_3$-$C_6$ cycloalkyl —C(=O)O($R^{13}$), —C(=O)N($R^{13}$) ($R^{14}$), —N($R^{13}$) ($R^{14}$) or hydroxyl, $C_1$-$C_4$ alkyl substituted with 0–4 groups selected from: $R^{11}$, =N($R^{14}$), =NN($R^{13}$)C(=O)N($R^{13}$)($R^{14}$) or —N($R^{13}$)($R^{14}$), $C_2$-$C_4$ alkenyl substituted with 0–4 $R^{11}$, $C_2$-$C_4$ alkynyl substituted with 0–4 $R^{11}$, a 5- or 6-membered heterocyclic ring containing from 1 to 4 heteroatoms independently selected from oxygen, nitrogen or sulfur, a 3- or 4-carbon chain attached to an adjacent carbon on the ring to which it is appended, to form a fused 5- or 6-membered ring, said 5- or 6-membered ring being optionally substituted on the aliphatic carbons with halogen, $C_1$-$C_4$ alkyl, $C_1$-$C_4$ alkoxy, hydroxyl, —N($R^{13}$)($R^{14}$), or when $R^{32}$ is attached to a saturated carbon atom, $R^{32}$ may be =O or =S;

Each $R^{32}$ when a substituent on nitrogen, is independently:
phenyl, phenylmethyl, phenethyl, hydroxyl, $C_1$-$C_4$ hydroxyalkyl, $C_1$-$C_4$ alkoxy, $C_1$-$C_4$ alkyl, $C_3$-$C_6$ cycloalkyl, $C_3$-$C_6$ cycloalkylmethyl, —CH$_2$N($R^{13}$) ($R^{14}$), —N($R^{13}$) ($R^{14}$), $C_2$-$C_6$ alkoxyalkyl, $C_1$-$C_4$ haloalkyl, $C_1$-$C_4$ alkoxycarbonyl, —C(=O)OH, $C_1$-$C_4$ alkylcarbonyloxy, $C_1$-$C_4$ alkylcarbonyl or —C($R^{14}$)=N—O($R^{14}$);

$R^{40}$ is: hydrogen or $C_1$-$C_3$ alkyl;
$R^{41}$ is: —C(=O)N($R^{13}$) ($R^{14}$), —C(=O)N($R^{13}$)NH($R^{14}$), —C(=O)C($R^{11}$)$_2$N($R^{13}$) ($R^{14}$), —C(=O)C($R^{11}$)$_2$N($R^{13}$)NH($R^{14}$), —C(=O)C($R^{11}$)$_2$N($R^{13}$)C(=O)O($R^{13}$), —C(=O)H, —C(=O) ($R^{11}$), —C(=O)—($C_1$-$C_4$ alkyl)—N($R^{13}$) ($R^{14}$), —C(=O)—($C_1$-$C_4$ alkyl)—N ($R^{13}$)C(=O)O($R^{13}$) or 1–3 amino acids linked together via amide bonds and linked to the N atom via the carboxylate terminus; and n is: 0 or 1;
provided that:
$R^4$, $R^{4A}$, $R^7$ and $R^{7A}$ are not all hydrogen;
when $R^4$ and $R^{4A}$ are both hydrogen, at least one of $R^{22}$, $R^{25}$ and $R^{26}$ is not hydrogen, and
when $R^7$ and $R^{7A}$ are both hydrogen, at least one of $R^{23}$, $R^{27}$ and $R^{28}$ is not hydrogen.

Another aspect of the invention is a method for treating viral infections which comprises administering to a host in need of such treatment a therapeutically effective amount of a compound of formula (I) or a pharmaceutically acceptable salt or prodrug form thereof.

A further aspect of the invention provides a pharmaceutical composition comprising a pharmaceutically acceptable carrier and a therapeutically effective amount of a compound of formula (I) or a pharmaceutically acceptable salt or prodrug form thereof.

DETAILED DESCRIPTION OF PREFERRED EMBODIMENTS DEFINITIONS

As used herein, the following terms and expressions have the indicated meanings.

"Alkenyl" is intended to include hydrocarbon chains of either a straight or branched configuration having one or more carbon-carbon double bonds which may occur at any point along the chain that results in a stable structure, with exemplary alkenyl groups being ethenyl, propenyl, and the like.

"Alkoxy" is intended to include an alkyl group of an indicated number of carbon atoms attached through an oxygen bridge to the residue of the compound at the designated location.

"Alkoxycarbonyl" is intended to include an alkoxy group of an indicated number of carbon atoms attached through its oxygen atom to a carbonyl bridge, where the bridge is attached to the residue of the compound at the designated location.

"Alkyl" is intended to include both branched and straight-chain saturated aliphatic hydrocarbon groups having the specified number of carbon atoms.

"Alkylcarbonyl" is intended to include an alkyl group of an indicated number of carbon atoms attached through a carbonyl group to the residue of the compound at the designated location.

"Alkylcarbonylamino" is intended to include an alkyl group of an indicated number of carbon atoms attached through a carbonyl group to an amino bridge, where the bridge is attached to the residue of the compound at the designated location.

"Alkylcarbonyloxy" is intended to include an alkyl group of an indicated number of carbon atoms attached to a carbonyl group, where the carbonyl group is attached through an oxygen atom to the residue of the compound at the designated location.

"Alkynyl" is intended to include hydrocarbon chains of either a straight or branched configuration having one or more carbon-carbon triple bonds which may occur at any point along the chain that results in a stable structure, where exemplary alkynyl groups are ethynyl, propynyl and the like.

"Amine protecting group" is intended to include any group known in the art of organic synthesis for the protection of amine groups. Such amine protecting groups include those listed in Greene et al. *Protective Groups in Organic Synthesis;* John Wiley & Sons: New York, 1991 and *The Peptides: Analysis, Synthesis, Biology;* Roberts et al. Eds.; Academic Press: New York, 1981; Vol. 3., the disclosures of which are hereby incorporated herein by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane types such as trimethylsilane; and (7) thiol containing types such as phenylthiocarbonyl and dithiasuccinoyl.

"Amino acid" is intended to include an organic compound containing both a basic amino group and an acidic carboxyl group. Included within this term are natural amino acids, modified and unusual amino acids, and amino acids which are known to occur biologically in free or combined form but usually do not occur in proteins. Among the modified and unusual amino acids are those disclosed in, for example, *The Peptides: Analysis, Synthesis, Biology;* Roberts et al. Eds.; Academic Press: New York, 1983; Vol. 5, p 342, the disclosure of which is hereby incorporated herein by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid and 2-benzyl-5-aminopentanoic acid.

"Amino acid residue" is meant to indicate that portion of an amino acid (as defined herein) that is present in a peptide.

"Any group that, when administered to a mammalian subject as part of a compound of formula (I), cleaves to form a free hydroxyl, free amino or free sulfhydryl" is intended to include an OH, $NH_2$ or SH group wherein a hydrogen atom is replaced with a masking group such that the O—, NH—, or S-masking group combination, when administered to a mammalian subject, cleaves to form a compound having a free hydroxyl (OH), free amino ($NH_2$), or free sulfhydryl (SH) group, respectively. Examples of masking groups include, but are not limited to, $C_1$-$C_6$ alkyl substituted with 0–3 $R^{11}$, $C_3$-$C_6$ alkoxyalkyl substituted with 0–3 $R^{11}$, $C_1$-$C_6$ alkylcarbonyl substituted with 0–3 $R^{11}$, $C_1$-$C_6$ alkoxycarbonyl substituted with 0–3 $R^{11}$, $C_1$-$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, amine protecting groups, hydroxyl protecting groups and sulfhydryl protecting groups, where the masking group is subject to enzymatic cleavage or cleavage by other conditions present within the mammalian subject. "Any group that, when administered to a mammalian subject as part of a compound of formula (I), cleaves to form a compound having two free hydroxyl groups, or two free amino groups, or one free hydroxyl and one free amino group", and "any group that, when administered to a mammalian subject as part of a compound of formula (I), cleaves to form a free hydroxyl" includes the O-masking group and NH-masking groups referred to above.

"Aryl" or "aromatic residue" is intended to include phenyl, naphthyl and biphenyl.

"$C_7$-$C_{10}$ arylalkyl" is intended to refer to an aryl group attached through a $C_1$-$C_4$ alkyl bridge to the residue of the indicated compound.

"($C_1$-$C_3$ alkyl)aryl" is intended to refer to a $C_1$-$C_3$ alkyl group which is attached through an aryl ring to the residue of the indicated compound.

"Aryl($C_1$-$C_3$ alkyl)" is intended to refer to an aryl group attached through a $C_1$-$C_3$ alkyl group to the residue of the indicated compound.

"Bicycloalkyl" is intended to include saturated bicyclic ring groups such as [3.3.0]bicyclooctane, [4.3.0]bicyclononane, [4.4.0]bicyclodecane(decalin), [2.2.2]bicyclooctane, and the like.

"Carbocycle" or "carbocyclic residue" or "carbocyclic ring system" is intended to include any stable 3- to 7-membered monocyclic or bicyclic ring, or any stable 7- to 14-membered bicyclic or tricyclic ring, or any stable polycyclic carbon ring having up to 26 members, any ring of which may be saturated, partially unsaturated, or aromatic. Examples of such carbocycles include, but are not limited to, cyclopropyl, cyclobutyl, cyclopentyl, cyclohexyl, phenyl, biphenyl, naphthyl, indanyl, adamantyl, and tetrahydronaphthyl (tetralin).

"Counterion" is intended to include small, negatively charged species such as chloride, bromide, hydroxide, acetate, sulfate, and the like.

"Cycloalkoxy" is intended to include cycloalkyl groups of indicated carbon number attached through an oxygen bridge to the designated position.

"Cycloalkyl" is intended to include saturated ring groups, including mono-, bi- and poly-cyclic ring systems, such as cyclopropyl, cyclobutyl, cyclopentyl, cyclohexyl, cycloheptyl, cyclooctyl and adamantyl. "Cycloalkylmethyl" is intended to include cycloalkyl groups of indicated carbon number attached through a methylene group to the designated position.

"Haloalkyl" is intended to include both branched and straight-chain saturated aliphatic hydrocarbon groups having the specified number of carbon atoms, substituted with 1 or more halogen atoms. "Halo" or "halogen" is intended to include fluoro, chloro, bromo, and iodo.

"Heterocycle" is intended to include stable 5- to 7-membered monocyclic or bicyclic rings and stable 7- to 10-membered bicyclic rings where the heterocycle may be either saturated or unsaturated, and where the heterocycle comprises from 1 to 4 heteroatoms independently selected from the group consisting of N, O and S, wherein the nitrogen and sulfur heteroatoms may optionally be oxidized, and the nitrogen heteroatom may optionally be quaternized, including a bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on a carbon or nitrogen atom if the resulting compound is stable. Examples of such heterocycles include, but are not limited to, acridinyl, azocinyl, benzimidazolyl, benzofuranyl, benzothiophenyl, carbazolyl, 4aH-carbazolyl, β-carbolinyl, chromanyl, chromenyl, cinnolinyl, decahydroquinolinyl, 2H, 6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindolinyl, isoindolyl, isoquinolinyl, isothiazolyl, isoxazolyl, morpholinyl, naphthyridinyl, octahydroisoquinolinyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, 4-piperidonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2-pyrrolidonyl, pyrrolinyl, pyrrolyl, 2H-pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, thianthrenyl, thienyl, thiophenyl, triazinyl and xanthenyl. Also included are fused ring and spiro compounds containing, for example, the above heterocycles.

"Hydroxy" and "hydroxyl" are used interchangeably, and both are intended to include the "—OH" group.

"Hydroxy protecting group" is intended to include any group known in the art of organic synthesis for the protection of hydroxyl groups. Such hydroxy protecting groups include those listed in Greene et al. *Protective Groups in Organic Synthesis;* John Wiley & Sons: New York, 1991, the disclosure of which is hereby incorporated herein by reference. Examples of hydroxy protecting groups include, without limitation, acyl types, aromatic carbamate types and alkyl types. Exemplary hydroxy protecting groups include, without limitation, methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

"Ketal group" or "ketal ring" is intended to include any ketal protecting group which can be hydrolyzed to form a carbonyl. Such ketal rings or ketal protecting groups are well known in the art of organic synthesis and typically include, for example, substituted or unsubstituted carbocyclic diethers, dithioethers, or mixed ethers. Such ketal protecting groups include those listed in Greene et al. *Protective Groups in Organic Synthesis;* John Wiley & Sons: New York, 1991.

"Peptide" is meant to include a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

"Peptide bond" means a covalent amide linkage formed by loss of a molecule of water upon the joining of the carboxyl group of a first amino acid and the amino group of a second amino acid.

"Pharmaceutically acceptable salt" is intended to include all derivatives of the subject compound wherein the compound is modified by formation of its acid or base salt. Examples of pharmaceutically acceptable salts include, but are not limited to, mineral or organic acid salts of basic residues such as amines. Examples of pharmaceutically acceptable salts also include, but are not limited to, alkali or organic salts of acidic residues such as carboxylic acids, and the like. Pharmaceutically acceptable salts of the compounds of the invention can be prepared, for example, by reacting the free acid or base forms of these compounds with a stoichiometric amount of the appropriate base or acid in water or in an organic solvent, or in a mixture of the two. Nonaqueous media like ether, ethyl acetate, ethanol, isopropanol, or acetonitrile are preferred. Lists of suitable salts are found in *Remington's Pharmaceutical Sciences* 1985, 1418 (17th ed., Mack Publishing Company, Easton, Pa.,) the disclosure of which is hereby incorporated herein by reference.

"Phosphite" is intended to include all compounds of formula (III) as set forth below.

"Phosphoramide" is intended to include all compounds of formula (I) as set forth below when the reference is to "bicyclic phosphoramides" and is intended to include all compounds of formula (IV) as set forth below when the reference is to "monocyclic phosphoramides".

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention effective to inhibit HIV infection or treat the symptoms of HIV infection in a host.

The compounds described herein may have asymmetric centers. All chiral, diastereomeric, and racemic forms of the compounds of formulas (I) through (XI), and of any other structural formulas present in Schemes 1 through 5 below, relating to the synthesis of the compounds, are intended. Compounds of the present invention containing an asymmetrically substituted atom may be isolated in optically active or racemic forms. It is well known in the art how to prepare optically active forms, such as by resolution of racemic forms or by synthesis from optically active starting materials.

The compounds described herein may have geometric isomers. All stable forms of geometric isomers of the compounds of formulas (I) through (XI), and of any other structural formulas present in Schemes 1 through 5 are intended. Geometric isomers include the geometric isomers of carbon—carbon double bonds, carbon-nitrogen double bonds, rings, and the like, including both cis and trans isomers. All chiral, diastereomeric, racemic forms and all geometric isomeric forms of a structure are intended, unless the specific stereochemistry or isomeric form is specifically indicated.

When any variable (e.g., $R^4$ through $R^{41}$, $R^{44}$ through $R^{24A}$, etc.) occurs more than one time in any constituent or in formulas (I) through (XI), or in any other formula herein, its definition on each occurrence is independent of its definition at any other occurrence. Thus, for example, if a group is substituted with 0–3 $R^{11}$, then said group may optionally be substituted with up to three $R^{11}$, and $R^{11}$ at each occurrence is selected independently from the defined list of possible $R^{11}$. Also, for example, in —N($R^{20}$)$_2$, each of the $R^{20}$ substituents may be independently selected from the list of possible $R^{20}$ groups defined. Also, combinations of substituents and/or variables are permissible only if such combinations result in stable compounds.

Compounds of the invention have the formula (I) where $R^4$, $R^{4A}$, $R^5$, $R^{5A}$, $R^6$, $R^{6A}$, $R^7$, $R^{7A}$, $R^8$, $R^{11}$, $R^{11A}$, $R^{12}$ when a substituent on either carbon or nitrogen, $R^{13}$, $R^{14}$, $R^{15}$, m, T, $R^{20}$, $R^{21}$, $R^{22}$, $R^{23}$, Z, $R^{24A}$, $R^{25}$, $R^{26}$, $R^{27}$, $R^{28}$, $R^{31}$, $R^{32}$ when a substituent on either carbon or nitrogen, $R^{40}$, $R^{41}$, and n are defined as provided in the preceding Summary of the Invention, with the proviso as also provided in the preceding Summary of the Invention. In addition to compounds of formula (I), compounds of the invention include pharmaceutically acceptable salt or prodrug forms thereof.

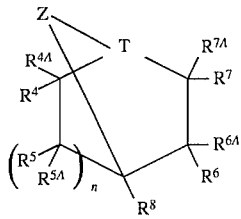

(I)

Preferred compounds include compounds of formula (I) or a pharmaceutically acceptable salt or prodrug form thereof wherein:

Each of $R^4$ and $R^7$ is independently:
  hydrogen or $C_1$-$C_3$ alkyl substituted with 0–1 $R^{11}$;
Both $R^{4A}$ and $R^{7A}$ are hydrogen;
$R^5$ is —$O(R^{20})$;
$R^{5A}$ is hydrogen;
$R^6$ is hydrogen or —$O(R^{21})$;
$R^{6A}$ is hydrogen;
$R^8$ is hydrogen;
$R^{11}$ is:
  hydrogen, halogen, —$O(R^{13})$, $C_3$-$C_{10}$ cycloalkyl, $C_1$-$C_4$ alkyl, aryl($C_1$-$C_3$ alkyl) substituted with 0–2 $R^{12}$; aryl substituted with 0–2 $R^{12}$, or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl or oxazolidinyl, where the heterocyclic ring system is substituted with 0–3 $R^{12}$;
Each $R^{12}$, when a substituent on carbon, is independently:
  phenylmethoxy, halogen, methyl, $C_1$-$C_4$ alkoxy, trifluoromethyl, 2-(1-morpholino)ethoxy, —C(=O)OH, hydroxamic acid, hydrazide, —C($R^{14}$)=N—O($R^{14}$), cyano, boronic acid, sulfonamide, formyl, $C_3$-$C_6$ cycloalkoxy, $C_1$-$C_4$ alkyl substituted with —N($R^{13}$) ($R^{14}$), —N($R^{13}$) ($R^{14}$), hydroxy or hydroxymethyl;
Each $R^{12}$, when a substituent on nitrogen, is methyl;
$R^{13}$ is: hydrogen, $C_1$-$C_4$ alkyl, $C_2$-$C_4$ alkenyl or phenylmethyl;
Each $R^{14}$ is independently:
  hydrogen, hydroxy, trifluoromethyl, $C_1$-$C_4$ alkyl, $C_1$-$C_4$ alkoxy, $C_2$-$C_4$ alkenyl, phenylmethyl or amino;
Each of $R^{20}$ and $R^{21}$ is independently:
  hydrogen or any group that, when administered to a mammalian subject as part of a compound of formula (I), cleaves to form a free hydroxyl;
Each of $R^{22}$ and $R^{23}$ is independently:
  hydrogen, $C_1$-$C_8$ alkyl substituted with 0–3 $R^{31}$, $C_2$-$C_6$ alkenyl substituted with 0–3 $R^{31}$, or $C_2$-$C_4$ alkynyl substituted with 0–3 $R^{31}$;
Z is: O or N($R^{24A}$);
$R^{24A}$ is: hydrogen or $C_1$-$C_6$ alkyl;
Each of $R^{25}$ and $R^{27}$ is independently:
  hydrogen, $C_1$-$C_4$ alkyl substituted with 0–3 $R^{31}$, or $C_3$-$C_4$ alkenyl substituted with 0–3 $R^{31}$;
Each of $R^{26}$ and $R^{28}$ is independently:
  hydrogen or halogen;
Each $R^{31}$ is independently:
  halogen, —$O(R^{13})$, $C_1$-$C_4$ alkyl, $C_3$-$C_{10}$ cycloalkyl, —$S(=O)_m(R^{13})$, —$C(R^{14})$=N—$O(R^{14})$, —$C(=O)O(R^{13})$, aryl substituted with 0–5 $R^{32}$, or
  a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl or oxazolidinyl, where the heterocyclic ring system is substituted with 0–2 $R^{32}$;
Each $R^{32}$, when a substituent on carbon, is independently:
  phenylmethoxy, halogen, 2-(1-morpholino)ethoxy, —$C(=O)O(R^{13})$, hydroxamic acid, —$C(=O)N(R^{13})N(R^{13})$ ($R^{14}$), cyano, boronic acid, sulfonamide, formyl, $C_3$-$C_6$ cycloalkoxy, —N($R^{13}$) ($R^{14}$), —$C(R^{14})$=N—$O(R^{14})$, —$NO_2$, —$O(R^{13})$, —N($R^{40}$) ($R^{41}$), —$S(=O)_m(R^{13})$, —$S(=O)_mN(R^{13})$ ($R^{14}$), —$C(=O)N(R^{13})$ ($R^{14}$), —$OC(=O)N(R^{13})$ ($R^{14}$), —$C(=O)$ ($R^{11}$), —$OC(=O)$ ($R^{11}$), —$OC(=O)O(R^{13})$, phenyl, —$C(=O)N(R^{13})$—($C_1$-$C_4$ alkyl)—N($R^{13}$) ($R^{14}$), —$C(=O)N(R^{40})$ ($R^{41}$), $C_1$-$C_4$ haloalkyl, $C_1$-$C_4$ haloalkoxy, $C_2$-$C_4$ haloalkenyl, $C_2$-$C_4$ haloalkynyl, —$C(=O)C(R^{11})_2N(R_{13})$ ($R^{14}$), —$C(=O)C(R^{11})_2N(R_{13})NH(R^{14})$, —$C(=O)C(R^{11})_2N(R_{13})C(=O)O(R^{13})$, —$C(=O)$—($C_1$-$C_4$ alkyl)—N($R^{13}$) ($R^{14}$), —$C(=O)$—($C_1$-$C_4$ alkyl)—N($R^{13}$)$C(=O)O(R^{13})$, $C_1$-$C_4$ alkoxy substituted with 0–3 groups selected from $R^{11}$, $C_3$-$C_6$ cycloalkyl, —$C(=O)N(R^{13})$ ($R^{14}$), —N($R^{13}$) ($R^{14}$) or hydroxyl,
  $C_1$-$C_4$ alkyl substituted with 0–3 groups selected from $R^{11}$, =N($R^{14}$), =NN($R^{13}$)$C(=O)N(R^{13})$ ($R^{14}$) or —N($R^{13}$) ($R^{14}$),
  $C_2$-$C_4$ alkenyl substituted with 0–3 $R^{11}$,
  $C_2$-$C_4$ alkynyl substituted with 0–3 $R^{11}$, or
  a 5- or 6-membered heterocyclic ring containing from 1 to 4 heteroatoms independently selected from oxygen, nitrogen or sulfur; and
Each $R^{32}$, when a substituent on nitrogen, is methyl.

Presently more preferred compounds of the invention include the compounds of formula (I) or a pharmaceutically acceptable salt or prodrug form thereof wherein:
Both $R^4$ and $R^7$ are phenylmethyl;
Both $R^{4A}$ and $R^{7A}$ are hydrogen;
$R^6$ is hydroxy;
$R^{6A}$ is hydrogen;
$R^8$ is hydrogen;
T is —N($R^{22}$)P(=O)N($R^{23}$)—;
Each of $R^{22}$ and $R^{23}$ is independently:
  hydrogen, allyl, methyl, ethyl, propyl, cyclopropylmethyl, n-butyl, i-butyl, pyridinylmethyl, methallyl, n-pentyl, i-pentyl, hexyl, phenylmethyl, isoprenyl, propargyl, methoxyethyl, cyclohexylmethyl, dimethylbutyl, ethoxyethyl, naphthylmethyl, methyloxazolinylmethyl, vinyloxyethyl, pentafluorophenylmethyl, quinolinylmethyl, carboxybenzyl, chloro-thienyl, benzyloxyphenylmethyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, dimethylallyl including —$CH_2CH=C(CH_3)_2$, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, (CH$_3$CH$_2$NHC(=O))-benzyl, N,N-diethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl—C(=O))-benzyl, (pyrazolyl—C(=O))-benzyl, (pyridylmethylaminocarbonyl)benzyl, (oxadiazolidinonyl)benzyl, trifluoroacetylbenzyl, (pyrazolyl)benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl—NHC(=O))O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C—C(=O))benzyl, (N-methyl—N-ethylaminoethyl)aminocarbonylbenzyl, (pyrrolidinylethyl)aminocarbonylbenzyl or (piperidinylethyl)aminocarbonylbenzyl;

Z is: O; and
n is: 0.

Still more presently preferred compounds of the invention are compounds of formula (I) or a pharmaceutically acceptable salt or prodrug form thereof wherein:
Both R$^4$ and R$^7$ are phenylmethyl;
Both R$^{4A}$ and R$^{7A}$ are hydrogen;
R$^6$ is hydroxy;
R$^{6A}$ is hydrogen;
R$^8$ is hydrogen;
T is —N(R$^{22}$)P(=O)N(R$^{23}$)—;
Both R$^{22}$ and R$^{23}$ are:

cyclopropylmethyl, n-butyl, 2-naphthalenylmethyl, phenylmethyl, 4-(hydroxymethyl)phenylmethyl, 3-(methylamino)phenylmethyl, 4-(hydroxy)phenylmethyl or 3-(hydroxymethyl)phenylmethyl);

Z is: O; and
n is: 0.

In the present invention it has been discovered that the compounds of formula (I) are useful as inhibitors of HIV protease and similar retroviral proteases, and are also useful for the treatment of HIV infection and similar retrovirus infections. The present invention provides a method for treating HIV infection by administering to a host infected with HIV a pharmaceutically or therapeutically effective or acceptable amount of a compound of formula (I).

The compounds provided by this invention are also useful as standards and reagents in determining the ability of a potential pharmaceutical to inhibit viral replication and/or HIV protease. These would be provided in a commercial kit comprising a compound provided by this invention.

SYNTHESIS

The compounds of the present invention can be prepared in a number of ways known to one skilled in the art. Preferred methods include, but are not limited to, the general synthetic procedures described below. Each of the references cited in this Synthesis section is hereby incorporated herein by reference.

Compounds of formula (I) may be prepared from diamines of formula (II), wherein the designations R$^4$, R$^{4A}$, R$^5$, R$^{5A}$, R$^6$, R$^{6A}$, R$^7$, R$^{7A}$, R$^8$, R$^{11}$, R$^{11A}$, R$^{12}$ when a substituent on either carbon or nitrogen, R$^{13}$, R$^{14}$, R$^{15}$, m, R$^{20}$, R$^{21}$, R$^{22}$, R$^{23}$, R$^{31}$, R$^{32}$ when a substituent on either carbon or nitrogen, R$^{40}$, R$^{41}$ and n are defined as provided in the preceding Summary of the Invention in connection with formula (I), Substituent M in formula (II) is selected so as to allow formation of group Z in formula (I), as described in detail below. It should be understood that diamines of formula (II) having n equal to 1 are precursors for the bicyclic phosphoramides of formula (I) having n equal to 1, and diamines of formula (II) having n equal to 0 are precursors for the bicyclic phosphoramides of formula (I) having n equal to 0.

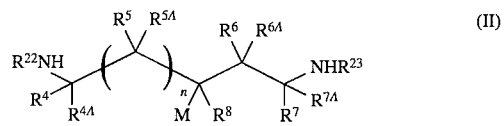

The diamines of formula (II) having n equal to 0 may be prepared as described in copending commonly assigned patent application Ser. No. 07/714,042 ("Jadhav et al."), filed May 31, 1991. Alternatively, synthetic methodology for preparing the diamines of formula (II) is found in U.S. Pat. Nos. 4,837,204 and 5,142,056, Canadian Patent Application No. 2,026,832 and in Baker et al. *J. Org. Chem.* 1993, 58, 3277. The diamines of formula (II) having n equal to 1 are conveniently prepared as described in Baker et al. *J. Org. Chem.* 1993, 58, 3277.

Compounds of formula (I) wherein T is —N(R$^{22}$)P(=O)N(R$^{23}$)— may be prepared from diamines of formula (II) according to several cyclization routes. For example, and as illustrated by pathway (a) of Scheme 1, treatment of the diamine of formula (IIa), having n equal to 0 and wherein M is OH, NH$_2$ or NH (R$^{24A}$), with phosphorous oxychloride in the presence of a base such as triethylamine, directly yields the bicyclic phosphoramide (Ia), corresponding to formula (I) wherein n is 0 and wherein Z is O, NH or N(R$^{24A}$) respectively.

An alternative cyclization route to compounds of formula (I) from the diamines of formula (II) proceeds through the bicyclic phosphite (III), wherein the designations R$^4$, R$^{4A}$, R$^5$, R$^5A$, R$^6$, R$^{6A}$, R$^7$, R$^{7A}$, R$^8$, R$^{11}$, R$^{11A}$, R$^{12}$ when a substituent on either carbon or nitrogen, $R^{13}$, $R^{14}$, $R^{15}$, m, $R^{20}$, $R^{21}$, $R^{22}$, $R^{23}$, Z, $R^{24A}$, $R^{25}$, $R^{26}$, $R^{27}$, $R^{28}$, $R^{31}$, $R^{32}$ when a substituent on either carbon or nitrogen, $R^{40}$, $R^{41}$, and n are defined as provided in the preceding Summary of the Invention in regard to formula (I). Substituent E in formula (III) is selected from the group consisting of —N($R^{22}$)PN($R^{23}$)—, —N($R^{22}$)PO—, —OPN($R^{23}$)—, —N($R^{22}$)PC($R^{27}$)C($R^{28}$)—, —C($R^{25}$)($R^{26}$)PN($R^{23}$)—, —N($R^{22}$)PS—, —SPN($R^{23}$)—, —C($R^{25}$)($R^{26}$)PC($R^{27}$)($R^{28}$)—, —C($R^{25}$)($R^{26}$)PO—, —OPC($R^{27}$)($R^{28}$)—, —C($R^{25}$)($R^{26}$)PS— and —SPC($R^{27}$)($R^{28}$)—.

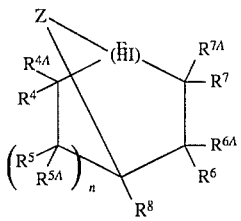

As illustrated as pathways (b) and (b') of Scheme 1, treatment of the diamine of formula (IIa) having n equal to 0 and wherein M is OH, $NH_2$ or N($R^{24A}$), with phosphorous trichloride yields a bicyclic phosphite (IIIa) wherein Z is O, NH or N($R^{24A}$), which can be oxidized to the corresponding bicyclic phosphoramide (Ia) by treatment with either a peracid such as m-chloroperbenzoic acid, or with nitrogen tetroxide. See, e.g., McGuigan et al. *Synthesis* 1993, 133.

An alternative synthetic route to selected compounds of formula (I) proceeds from the diamine of formula (II) through the monocyclic phosphoramide of formula (IV) wherein the designations $R^4$, $R^{4A}$, $R^5$, $R^{5A}$, $R^6$, $R^{6A}$, $R^7$, $R^{7A}$, $R^8$, $R^{11}$, $R^{11A}$, $R^{12}$ when a substituent on either carbon or nitrogen, $R^{13}$, $R^{14}$, $R^{15}$, m, $R^{20}$, $R^{21}$, $R^{22}$, $R^{23}$, $R^{25}$, $R^{26}$, $R^{27}$, $R^{28}$, $R^{31}$, $R^{32}$ when a substituent on either carbon or nitrogen, $R^{40}$, $R^{41}$, M and n are as defined previously. Substituent G in formula (IV) is selected from the group consisting of —N($R^{22}$)P(=O)(Q)N($R^{23}$)—, —N($R^{22}$)P(=O)(Q)O—, —OP(=O)(Q)N($R^{23}$)—, —N($R^{22}$)P(=O)(Q)C($R^{27}$)(C$R^{28}$)—, —C($R^{25}$)($R^{26}$)P(=O)(Q)N($R^{23}$)—, —N($R^{22}$)P(=O)(Q)S—, —SP(=O)(Q)N($R^{23}$)—, —C($R^{25}$)($R^{26}$)P(=O)(Q)C($R^{27}$)($R^{28}$)—, —C($R^{25}$)($R^{26}$)P(=O)(Q)O—, —OP(=O)(Q)C($R^{27}$)($R^{28}$)—, —C($R^{25}$)($R^{26}$)P(=O)(Q)S—, and —SP(=O)(Q)C($R^{27}$)($R^{28}$)—.

Substituent Q in formula (IV) is selected from leaving groups typically employed in organic synthesis, as illustrated in detail below, and include, without limitation, methoxy, ethoxy, phenoxy, benzyloxy, trichloroethoxy, 2,5-dichlorophenoxy, 2-bromophenoxy, N,N-dimethylamino and N,N-diethylamino.

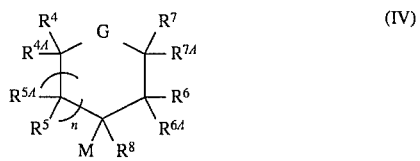

The conversion of the monocyclic phosphoramides of formula (IV) to the bicyclic phosphoramides of formula (I) can be achieved according to several synthetic routes. For example, treatment of a solution of the monocyclic phosphoramide (IV) wherein M is OH and Q is phenoxy, in a mixture of water and an organic solvent, e.g., tetrahydrofuran or dioxane, and with a slight excess of a dilute aqueous base, e.g., aqueous lithium hydroxide, sodium hydroxide or potassium hydroxide solution, at or above room temperature, affords the corresponding bicyclic phosphoramide of formula (I) wherein Z is O.

Where M in formula (IV) is a protected hydroxyl group, the protective group should be selected from among groups readily removed under mild conditions, e.g., mild acid, mild base or fluoride ion. One class of exemplary M groups is the silyloxy group, of which trimethylsilyloxy, triethylsilyloxy, triisopropylsilyloxy, and dimethyl-t-butylsilyloxy are representative. Compounds of formula (IV) wherein M is a silyloxy group are readily converted to the corresponding phosphoramide of formula (I) by treatment with fluoride ion, provided, for example, by tetra-n-butylammonium fluoride in tetrahydrofuran. Another class of exemplary M groups is the alkoxy group, where alkoxy groups that are readily converted to a OH group by treatment with mild acid are particularly preferred. Illustrative M groups wherein M is an alkoxy group include 2-t-butoxyethoxymethoxy, trimethylsilylethoxymethoxy and ketals such as diisopropylidene ketal.

Where M is an amino group, or NH($R^{24A}$), cyclization of the monocyclic phosphoramide (IV) to a bicyclic phosphoramide of the invention can be effected by treatment with a strong base, e.g., sodium hydride, in a suitable solvent, e.g., N,N-dimethylformamide or tetrahydrofuran.

Formation of the monocyclic phosphoramide of formula (IV) can be achieved from the diamine of formula (II) via several synthetic routes, two of which are illustrated in Scheme 2. For example, as shown along pathway (a), treatment of the diamine of formula (II) with a dichlorophosphate in the presence of base at between about 0° C. and about room temperature in a suitable solvent such as tetrahydrofuran or methylene chloride affords the corresponding monocyclic phosphoramide (IVa) wherein M is protected hydroxyl or amine group. See Patois et al. *Heteroatom. Chem.* 1990, 1(5), 369. Exemplary dichlorophosphates include ethyl dichlorophosphate, methyl dichlorophosphate and phenyl dichlorophosphate. Exemplary bases include organic bases such as triethylamine, diisopropylethylamine and N-methylmorpholine. A phosphoramidodichloridate, such as dimethylphosphoramidodichloridate may be used in place of the dichlorophosphate.

An alternative route to convert diamines of formula (II) to monocyclic phosphoramides of formula (IVa) is to replace the dichlorophosphate or phosphoramidodichloridate in the procedure described above with phosphorous oxychloride. As illustrated in pathways (b) and (b') of Scheme 2, this approach provides an intermediate monocyclic phosphoramide of formula (IVb), which can be converted to the monocyclic phosphoramides of formula (IVa) by reaction with a dialkylamine or an alkyl or aryl alcohol. See Peyronel *J. Org. Chem.* 1987, 52, 5320.

Compounds of formula (I) wherein T is —N($R^{22}$)P(=O)N($R^{23}$)—, and one or both of $R^{22}$ and $R^{23}$ is not hydrogen, can be prepared according to standard N-alkylation chemistry from the corresponding monocyclic or bicyclic phosphoramides wherein either $R^{22}$ or $R^{23}$ are hydrogen. For example, and as illustrated by pathways (a) and (a') of Scheme 3 for representative compounds of the invention, treatment of the compound of formula (IVc) wherein both $R^{22}$ and $R^{23}$ are hydrogen, with a strong base and in the presence of an alkylating agent such as benzyl bromide, provides the corresponding bis N-alkylated monocyclic phosphoramide of formula (IVd). The monocyclic phosphoramide of formula (IVd) can be converted to the corresponding bicyclic phosphoramide of formula (Ib) according to procedures described previously.

Alternatively, as illustrated by pathways (b) and (b') of Scheme 3, the monocyclic phosphoramide (IVc) can be converted directly to the bicyclic phosphoramide of formula (Ic), and then the bicyclic phosphoramide may be alkylated at the N-position with strong base and an alkylating agent such as benzyl bromide to give the alkylated bicyclic phosphoramide of formula (Ib). Under preferred reaction conditions, the strong base is sodium hydride, the alkylating agent has the structural formula $R^{22}X$ or $R^{23}X$ wherein X is a standard leaving group typically employed in synthetic organic chemistry, e.g., halide, triflate, tosylate or mesylate, and is preferably bromide or iodide, the alkylation is run at a temperature of between about 0° C. and about 100° C., and the solvent is a polar aprotic solvent, e.g., N,N-dimethylformamide of 1,3-dimethyl-3,4,5,6-tetrahydro-1(H)-pyrimidinone.

Compounds of formula (I) wherein T is $-N(R^{22})P(=O)O-$ or $-OP(=O)N(R^{23})-$ are conveniently prepared from diamines of formula (II) via intermediate aminoalcohols of formula (Va) and (Vb) respectively, wherein the substituent designations are the same as provided in connection with the diamines of formula (II).

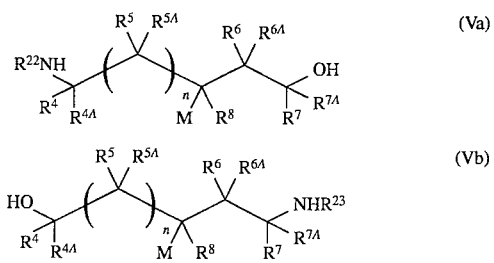

The aminoalcohol of formula (Va) or (Vb) may be prepared from the corresponding diamine of formula (II) through conversion of an amino group to a hydroxy group. This conversion may be accomplished by diazotization followed by hydrolysis, as described in March *Advanced Organic Chemistry; Reactions, Mechanisms and Structures* 1985 (3rd ed.) 348 (John Wiley & Sons, New York). Conversion of a hydroxy group to an amino group can also be achieved by treatment with an imide, such as phthalimide, in the presence of diethylazidodicarboxylate and triphenylphosphine, as described by Mitsunobu (*Synthesis* 1981, 1). Alternatively, the aminoalcohols of formula (Va) and (Vb) may be prepared from the corresponding dihydroxy compound by reaction with a single equivalent of azide followed by reduction of the intermediate azidoalcohol as described in Jadhav et al. supra.

The aminoalcohols of formulas (Va) and (Vb) may be converted to bicyclic phosphoramides of formula (I) according to the same general procedures previously outlined for converting diamines of formula (II) to bicyclic phosphoramides of formula (I), e.g., directly, or through the phosphite (III), or through the monocyclic phosphoramide (IV). In a preferred approach, aminoalcohols of formulas (Va) or (Vb) are reacted with phenyl dichlorophosphate in the presence of 2.2 eq of an organic base such as triethylamine, to obtain either the corresponding bicyclic phosphoramide of formula (I) or, when M is a protected hydroxy or amino group, a monocyclic phosphoramide of formula (IV) which can be converted to the bicyclic phosphoramide after deprotection of the hydroxy or amino group as described previously.

Compounds of formula (I) wherein T is $-N(R^{22})P(=O)S-$ or $-SP(=O)N(R^{23})-$ are conveniently prepared from diamines of formula (II) by diazotization of one of the amino groups followed by treatment with sodium hydrosulfide hydrate to give the corresponding aminothiol compound. See, e.g., March *Advanced Organic Chemistry; Reactions, Mechanisms and Structures* 1985 (3rd ed.) 601 (John Wiley & Sons, New York). Cyclization of the resulting aminothiol compound to a bicyclic phosphoramide of formula (I) may be accomplished by any of the synthetic methods already detailed in regard to cyclization of a diamine of formula (II) to a bicyclic phosphoramide of formula (I).

The aminoalcohols of formulas (Va) and (Vb) may also serve as convenient precursors for the synthesis of compounds of formula (I) wherein T is $-N(R^{22})P(=O)C(R^{27})(R^{28})-$ or $-C(R^{25})(R^{26})P(=O)N(R^{23})-$, respectively. As illustrated in Scheme 4, and starting from representative aminoalcohol of formula (Vc) having n equal to 0 and a protected amino group designated D, (see, e.g., Greene *Protecting Groups in Organic Synthesis* 1991, Chapter 2, John Wiley & Sons, New York, N.Y. for typical amine protecting groups which may be employed to prepare the protected amine group D) (Vc) may be converted to the corresponding aminobromide of formula (VI) according to Morin et al. *Synthesis* 1987, 479. Displacement of the bromide by the lithium salt of dimethyl methylphosphonate to afford the aminophosphonate of formula (VII) (See, e.g., Corey et al. *J. Am. Chem. Soc.* 1966, 88, 5654); Removal of the amine protecting group to yield a primary amine of formula (VIII) (see Greene, supra), followed by phosphoramide formation (see, e.g., Patel et al. *Tet. Let.* 1990, 31, 5591) would provide the bicyclic phosphoramides of formula (Id) in instances where M is OH, $NH_2$ or $NH(R^{24A})$. When M is a protected alcohol or amine group, cyclization of the aminophosphonate of formula (VIII) would provide a monocyclic phosphoramide of formula (IVe), which upon deprotection to convert M to OH, $NH_2$ or $NH(R^{24A})$, may be reacted with base to form the bicyclic phosphoramide of formula (Id). As further illustrated in Scheme 4, modification of the $R^{22}$, $R^{23}$, $R^{25}$, $R^{26}$, $R^{27}$ or $R^{28}$ groups can be achieved through alkylation of the corresponding $-NH-$ or $-CH_2-$ group of either the monocyclic or bicyclic phosphoramides along pathways (a), (b) and (c) of Scheme 4, in an analogous fashion to the procedures illustrated in Scheme 3.

Compounds of formula (I) wherein T is $-OP(=O)C(R^{27})(R^{28})-$ or $-C(R^{25})(R^{26})P(=O)O-$ may be prepared from the aminophosphonates (VIII) by diazotization of the amino group, and nucleophilic displacement of the azide group with sodium hydroxide to give the corresponding hydroxyphosphonates. The hydroxyphosphonates may be cyclized to bicyclic phosphoramides of formula (I) by any of the cyclization methods described previously. Compounds of formula (I) wherein T is $-SP(=O)C(R^{27})(R^{28})-$ or $-C(R^{25})(R^{26})P(=O)S-$ may likewise be prepared from the aminophosphonates (VIII) by diazotization of the amino group, and nucleophilic displacement of the azide group with sodium hydrosulfide to give the corresponding thiophosphonates. The thiophosphonates may be cyclized to bicyclic phosphoramides having formula (I) by any of the cyclization methods described previously.

Compounds of formula (I) wherein T is $-C(R^{25})(R^{26})P(=O)C(R^{27})(R^{28})-$ may be prepared from a dihydroxy compound of formula (IX), where the designations $R^4$, $R^{4A}$, $R^5$, $R^{5A}$, $R^6$, $R^{6A}$, $R^7$, $R^{7A}$, $R^8$, $R^{11}$, $R^{11A}$, $R^{12}$ when a substituent on either carbon or nitrogen, $R^{13}$, $R^{14}$, $R^{15}$, m, $R^{20}$, $R^{21}$ and n are defined as provided in the preceding Summary of the Invention in connection with formula (I). Substituent M in formula (IX) has been described in connection with formula (II).

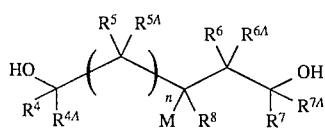

As shown in Scheme 5 for a representative dihydroxy compound of formula (IXa), a dihydroxy compound may be brominated by the method of Morin et al. supra to give a dibromide of formula (X) which may be elaborated to a diphosphonate of formula (XI) by reaction with two equivalents of the lithium salt of dimethyl methylphosphonate. Grignard coupling of the diphosphonate of formula (XI) with methyl dichlorophosphate using the method of Polniaszek et al. *J. Org. Chem.* 1991, 56, 3137, may provide a bicyclic phosphoramide of formula (Ie) or a monocyclic phosphoramide of formula (IVf), depending on the identify of the group M as described previously. Subsequent modification of the substituents $R^{22}$, $R^{23}$, $R^{25}$, $R^{26}$, $R^{27}$ or $R^{28}$ groups can be achieved through alkylation of the corresponding —$CH_2$— group of either the monocyclic or bicyclic phosphoramides, as described previously. See, e.g. Polniasek, supra.

Compounds of formula (I) wherein T is:

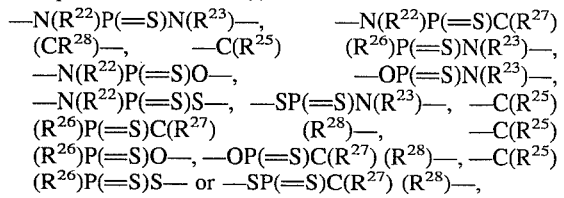

may be synthesized from the corresponding compounds of formula (I) having a P(=O) functional group by reaction with elemental sulfur, phosphorous pentasulfide or Lawesson's reagent to effect the oxygen-sulfur exchange. See, e.g., Horner, et al. *Phosphorous Sulfur* 1982, 12(2), 259 and Yousif et al. Phosphorous Sulfur 1991, 60(3–4), 261.

Compounds of formula I wherein T is —N($R^{22}$)P(=S)N($R^{23}$)—, —N($R^{22}$)P(=S)O—, —OP(=S)N($R^{23}$)—, —N($R^{22}$)P(=S)S— or —SP(=S)N($R^{23}$)— may alternatively be prepared by reaction of a thiophosphate, such as ethyl dichlorothiophosphate, with either a diamine of formula (II), or an aminoalcohol or aminothiol derived therefrom, to yield a monocyclic phosphoramide of formula (IV) where the latter may be cyclized to the corresponding bicyclic compound of formula (I) by the cyclization techniques described previously.

Compounds of formula (I) wherein T is

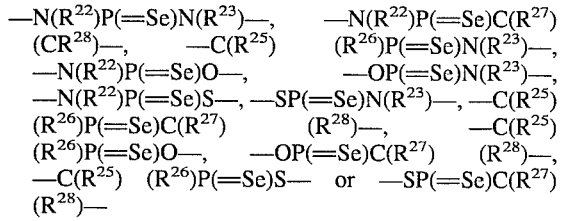

may be prepared from the corresponding bicyclic phosphite compounds of formula (III) wherein E is

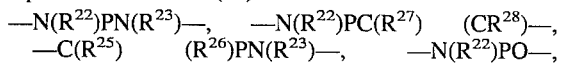

respectively, by treatment with selenium metal in an appropriate solvent, e.g., methylene chloride, dioxane or benzene. See, e.g., Kaukorat et al. *Z. Naturforsch., B. Chem. Sci.* 1992, 47(2), 275. The phosphite derivatives may be prepared as described previously, e.g., by reacting the diamine of formula (II) having M equal to OH, $NH_2$, or $NHR^{24A}$ with phosphorous trichloride or phosphorous tribromide.

Polyhydroxylated compounds, e.g., sugars and sugar derivatives, are convenient precursors to the diamines of formulas (II), the aminoalcohols of formula (Va) and (Vb), and the dihydroxy compounds of formula (IX). The following synthetic methodology for manipulating the hydroxyl group is therefore advantageously employed in preparing the bicyclic phosphoramides of formula (I), and precursors thereof.

Conversion of a hydroxy group to selected —O($R^{13}$), —O($R^{20}$) or —O($R^{21}$) groups may be achieved by reaction with one equivalent of base followed by one equivalent of acyl halide, alkyl halide, alkoxyalkyl halide, alkoxycarbonyl halide, benzoyl halide, diphenyl carbonate or phenylisocyanate.

Conversion of a hydroxy group to a hydrogen group may be achieved by derivatization of the hydroxy and reduction with a trialkyltin hydride according to procedures described in Robins et al. *J. Am. Chem. Soc.* 1981, 103, 932.

Conversion of a hydroxy group to a fluoride group may be achieved by reaction with a fluorinating agent, preferably diethylaminosulfurtrifluoride (DAST). See *Reagents for Organic Synthesis* 1988, 13, 110 (Wiley Interscience, New York N.Y.).

Conversion of a hydroxy group to a ketone group may be achieved according to standard oxidative procedures, and preferably with oxalyl chloride and triethylamine in dimethylsulfoxide (Swern oxidation). See, e.g., Manacuso and Swern *Synthesis* 1981, 165 and Tidwell *Synthesis* 1990, 857.

Conversion of a primary or secondary hydroxyl group to a difluoromethylene group may be achieved by preparing an intermediate ketone (see, e.g., Swern oxidation, supra) followed by reaction of the carbonyl with a fluorinating reagent, e.g., DAST.

Conversion of a primary or secondary hydroxyl group to a $C_1$-$C_8$ alkyl group may be achieved by preparing an intermediate ketone (see, e.g., Swern oxidation, supra) followed by olefination according to methods well known to one skilled in the art (see, e.g., Larock *Comprehensive Organic Transformations,* 1988 73–184), followed by reduction of the resulting alkene according to methods well known to one skilled in the art (see, e.g., Larock *Comprehensive Organic Transformations* 1989 6–17).

During synthesis of the bicyclic phosphoramides of formula (I), it is frequently advantageous to protect hydroxyl and/or amino groups while conducting reactions at other sites of the molecule. Suitable protecting groups are disclosed in Greene et al. *Protective Groups in Organic Synthesis,* John Wiley & Sons, New York, 1991, Chap 2.

SCHEME 1
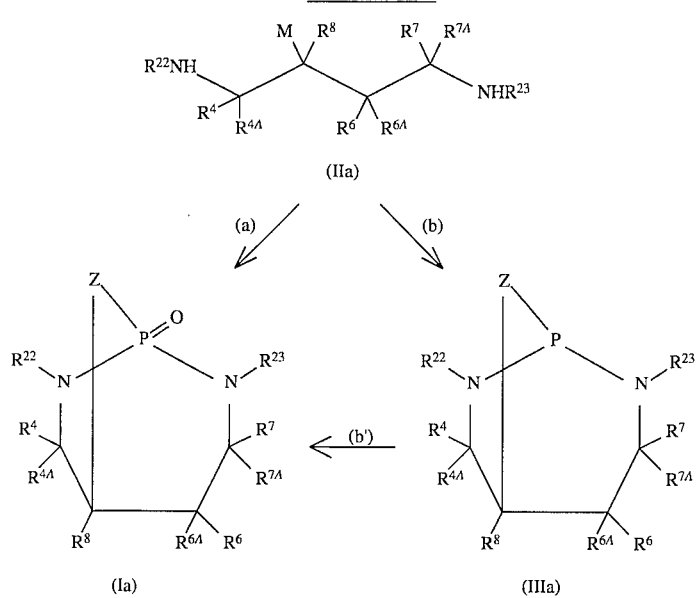
SCHEME 2
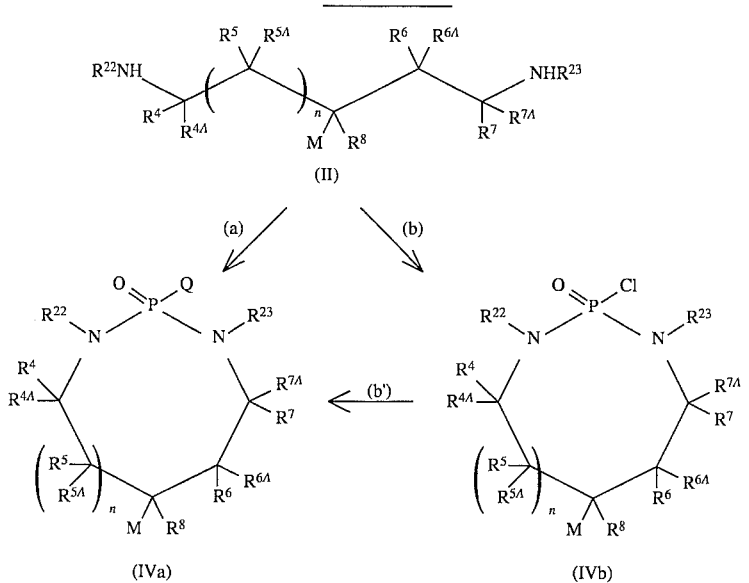

SCHEME 3
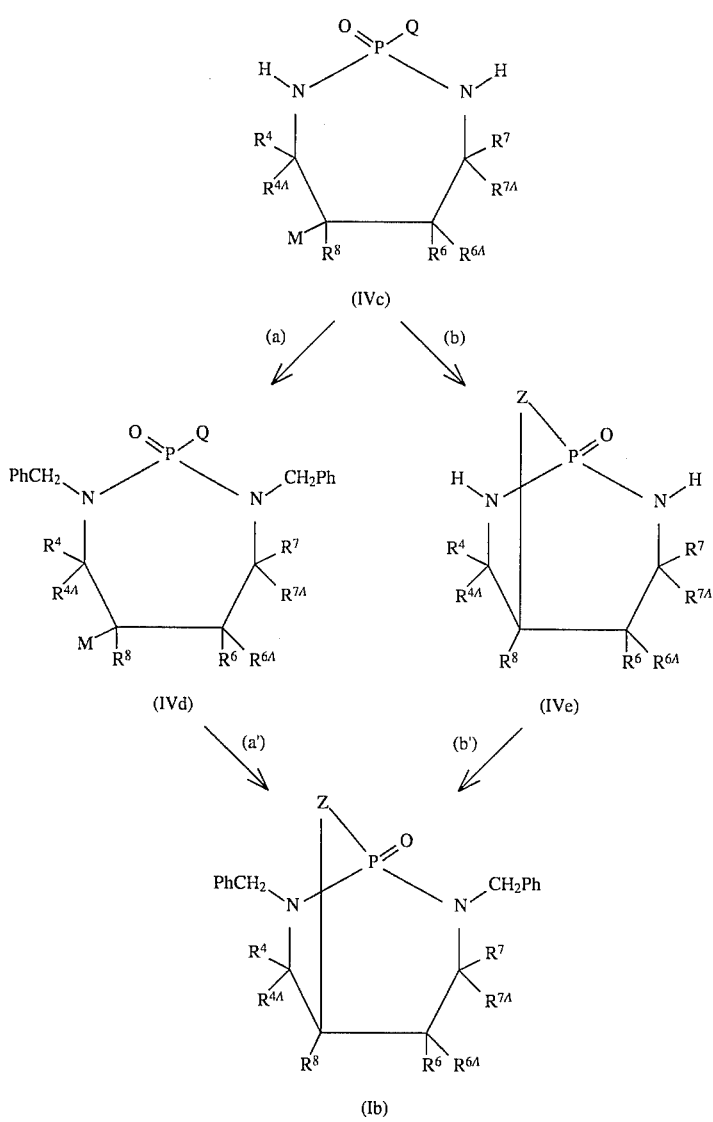
SCHEME 4
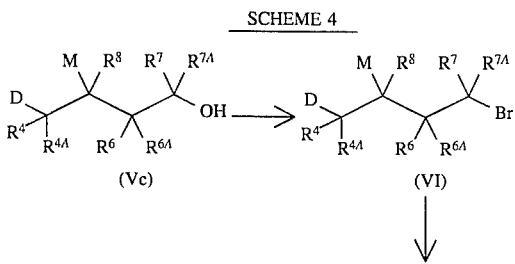
-continued
SCHEME 4
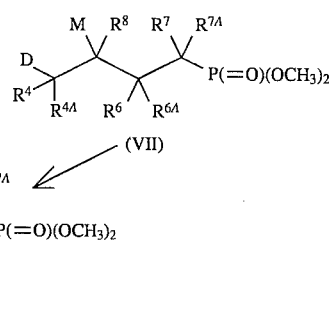

-continued
SCHEME 4

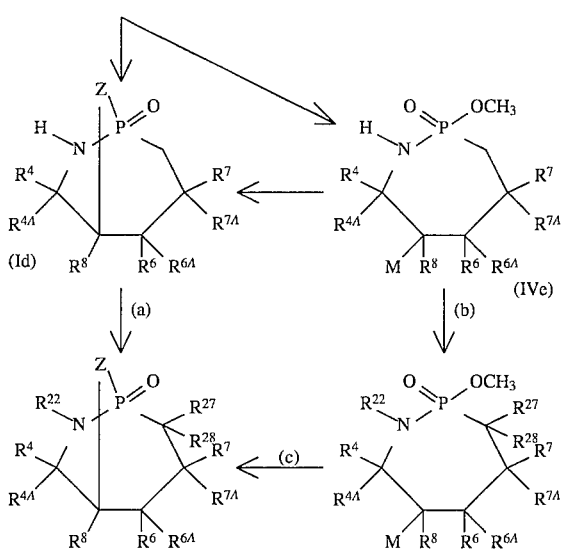

SCHEME 5

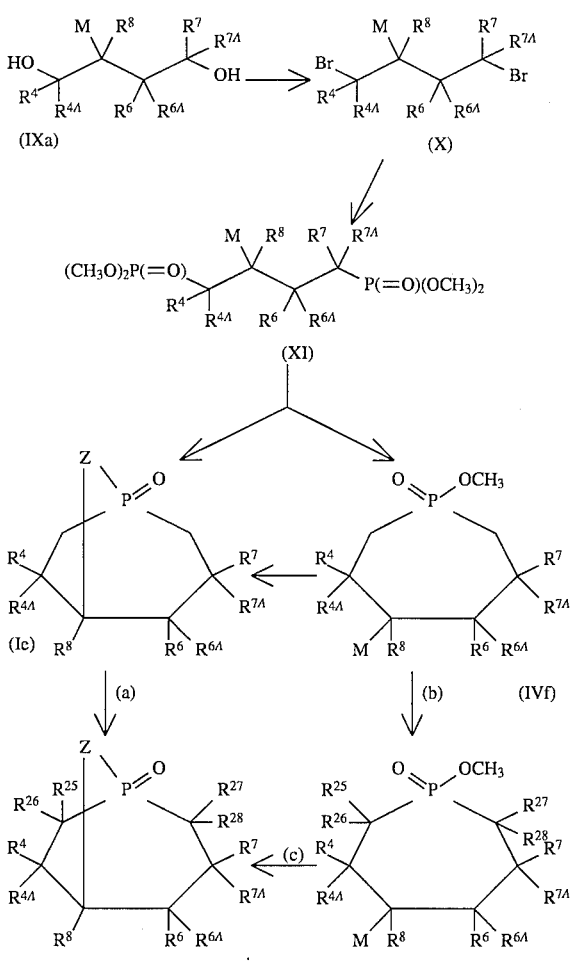

EXAMPLES

The synthesis of representative compounds according to the invention is described in further detail below with reference to the following specific, but non-limiting examples.

Abbreviations used in the Examples are defined as follows: "1X" for once, "2X" for twice, "3X" for thrice, "bs" for broad singlet, "° C." for degrees Celsius, "Cbz" for benzyloxycarbonyl, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "$^1$H" for proton, "hr" for hour or hours, "m" for multiplet, "M" for molar, "min" for minute or minutes, "mp" for melting point range, "MHz" for megahertz, "MS" for mass spectroscopy, "nmr" or "NMR" for nuclear magnetic resonance spectroscopy, "SEM" for 2-(trimethylsilyl)ethoxymethyl, "SEM-Cl" for 2-(trimethylsilyl)ethoxymethyl chloride, "t" for triplet, "tlc" for thin layer chromatography, "v/v" for volume to volume ratio. "α", "β", "R" and "S" are stereochemical designations familiar to those skilled in the art.

Example 1

A. (2R,3S,4S,5R)-2,5-Bis(N-Cbz-amino)-1,6-diphenyl-3,4-(1-methylethylidene)bis(oxy)hexane.

To a suspension of 10 g of (2R,3S,4S,5R)-2,5-bis-(N-Cbz-amino)-3,4-(dihydroxy)-1,6-diphenylhexane in 200 mL of methylene chloride was added 10.8 mL of 2,2-dimethoxypropane and 0.41 g of camphorsulfonic acid. The mixture was stirred at room temperature for 48 hr, then washed successively with saturated sodium hydrogen carbonate solution and saturated sodium chloride solution. The organic phase was dried over anhydrous magnesium sulfate and concentrated on a rotary evaporator. The residue was crystallized from ether/hexane (1/10 v/v) to give 6.6 g (60% yield) of the title compound as white needles, mp 76°–77° C.

B. (2R,3S,4S,5R)-2,5-Diamino-1,6-diphenyl-3,4-(1-methylethylidene)bis(oxy)hexane.

To a solution of 6.6 g of the compound prepared in Example 1A in 100 mL of tetrahydrofuran/ethanol (1/1 v/v) was added 0.7 g of 10% Pd/C. The mixture was stirred vigorously under 1 atmosphere of hydrogen gas for 18 hr. The catalyst was isolated by filtration and washed with tetrahydrofuran. The combined filtrate and washings were concentrated on a rotary evaporator. The residue consisted of 3.6 g (100% yield) of the title compound, which was used without further purification in the procedure of Example 1C.

C. (4α,5α,6β,7β)-Hexahydro-5,6-(1-methylethylidene)bis-(oxy)-2-phenoxy-4,7-bis(phenylmethyl)-1H-1,3,2-diazaphosphepine 2-oxide.

To a solution of 2 g of the compound prepared in Example 1B in 15 mL of anhydrous tetrahydrofuran, maintained at 0°–10° C. under a nitrogen atmosphere with efficient stirring, was added 1.8 mL (2.2 eq) of triethylamine followed by dropwise addition of a solution of 0.9 mL (1 eq) of phenyldichlorophosphate in 4 mL of tetrahydrofuran. The mixture was stirred for 16 hr at room temperature. The resulting triethylamine hydrochloride was isolated by filtration and washed with tetrahydrofuran. The combined filtrate and washings were concentrated on a rotary evaporator, taken up in methylene chloride/ethyl ether (1/1 v/v), and washed successively with water (2X), and saturated sodium chloride solution (1X). After drying over anhydrous magnesium sulfate, the organic layer was concentrated on a rotary evaporator. Purification of the residue by column chromatography using a short pad of silica gel eluting with hexane/ ethyl acetate (1/1 v/v) gave 1.8 g (64% yield) of the title compound as a sticky white foam.

D. 1,3-Bis(cyclopropylmethyl)-(4α,5α,6β,7β)-hexahydro-5,6-(1-methylethylidene)bis(oxy)-2-phenoxy-4,7-bis(phenylmethyl)-1H-1,3,2-diazaphosphepine 2-oxide.

To a solution of 0.1 g of the compound prepared in Example 1C in 3 mL of anhydrous N,N-dimethylformamide, maintained under a nitrogen atmosphere at room temperature, was added 35 mg of 60% NaH (by weight, dispersed in oil). The mixture was stirred for 10–15 min followed by addition of 0.16 mL bromomethylcyclopropane. The mixture was stirred for 48 hr at room temperature, then quenched by water addition. The product was extracted with ethyl acetate (3X). The combined extracts were washed successively with water (2X) and saturated sodium chloride solution (1X), dried over anhydrous magnesium sulfate, and concentrated on a rotary evaporator. The residue was purified using rotary preparative tlc eluting with hexane/ethyl acetate (4/1 v/v) to give 97 mg (79% yield) of the title compound as an amber oil.

E. 1,3-Bis(cyclopropylmethyl)-(4α,5α,6β,7β)-hexahydro-2-phenoxy-4,7-bis(phenylmethyl)-1H-1,3,2-diazaphosphepine 2-oxide.

To a solution of 97 mg of the compound prepared in Example 1D in 2 mL of anhydrous methylene chloride, maintained under an argon atmosphere at −78° C., was added 0.5 mL of a 2.0M solution of dimethylboron bromide in methylene chloride by dropwise addition. The addition was completed in 10–15 min, and the mixture was thereafter stirred for 1 hr at −78° C. The mixture was then transferred via syringe to a rapidly stirring mixture of 1 mL tetrahydrofuran and 0.5 mL aqueous saturated sodium hydrogen carbonate solution. After stirring for 5 min, the mixture was extracted with ethyl acetate (3X). The combined extracts were washed successively with 10% aqueous potassium hydrogen sulfate solution and saturated sodium chloride solution. After drying over anhydrous magnesium sulfate, the organic layer was concentrated by rotary evaporation. The residue was purified by rotary preparative tlc eluting with hexane/ethyl acetate (4/1 v/v) to give 70 mg (78% yield) of the title compound as an amorphous white solid.

F. (3-endo,4-endo,6-exo)-2,7-Bis(cyclopropylmethyl)-3,6-bis(phenylmethyl)-8-oxa-2,7-diaza-1-phosphabicyclo[3.2.1]octan-4-ol 1-oxide.

To a solution of 58 mg of the compound prepared in Example 1E in 2 mL of tetrahydrofuran/water (3/1 v/v) was added 0.22 mL of 1M aqueous lithium hydroxide. The mixture was heated for 2 hr with stirring in a 65°–70° C. oil bath under a nitrogen atmosphere. After cooling to room temperature, the mixture was extracted with diethyl ether (3X). The combined ether extracts were washed with saturated sodium chloride solution, dried over anhydrous magnesium sulfate, and then concentrated by rotary evaporation. Purification of the residue using preparative tlc eluting with hexane/ethyl acetate (65/35 v/v) gave 33 mg (69% yield) of the title compound as a white solid, mp 167°–169° C. $^1$H NMR (300 MHz, CDCl$_3$) δ: 0.00 (1H,m) 0.10 (1H,m) 0.34 (4H,m) 0.65 (2H, d) 0.76 (1H,m) 1.19 (1H, m) 2.07 (1H,m) 2.48 (1H,bs) 2.66 (1H, dd) 2.83 (1H, dd) 3.01 (2H,m) 3.22 (2H,m) 3.41 (1H, dd) 3.72 (2H,m) 4.26 (1H, dd) 4.29 (1H, m) 7.16–7.37 (10H, m). MS m/z 453 (M+H)$^+$.

Example 2

A. (4α,5β,6β,7β)-Hexahydro-5,6-(1-methylethylidene)bis-(oxy)-1,3-bis(2-naphthalenylmethyl)-2-phenoxy-4,7-bis(phenylmethyl)-1H-1,3,2-diazaphosphepine 2-oxide.

Using the procedure of Example 1D, but replacing the bromomethylcyclopropane with 2-bromomethylnaphthalene gave the title compound in 50% yield.

B. 5,6-Dihydroxy-(4α,5α,6β,7β)-hexahydro-1,3-bis(2-naphthalenylmethyl)-2-phenoxy-4,7-bis(phenylmethyl)-1H-1,3,2-diazaphosphepine 2-oxide.

Using the procedure of Example 1E, but replacing the compound prepared in Example 1D with the compound prepared in Example 2A gave the title compound in 66% yield.

C. (3-endo,4-endo,6-exo)-2,7-Bis(2-naphthalenylmethyl)-3,6-bis(phenylmethyl)-8-oxa-2,7-diaza-1-phosphabicyclo[3.2.1]octan-4-ol 1-oxide.

Using the procedure of Example 1F, but replacing the compound prepared in Example 1E with the compound prepared in Example 2B gave a low yield of the title compound. Recrystallization from methylene chloride/hexane (1/4 v/v) gave needles, mp 131°–132° C. $^1$H NMR (300 MHz, CDCl$_3$) δ: 1.43 (1H,d) 2.54 (1H,dd) 2.72 (2H,m) 3.24 (2H,m) 3.54 (1H,m) 3.78 (2H,m) 4.15 (1H,dd) 4.38 (1H,dd) 4.74 (1H,dd) 5.03 (1H,dd) 7.00 (2H, d) 7.10 (1H,t) 7.18 (2H,t) 7.30 (6H,m) 7,39 (1H,s) 7.46 (5H,m) 7.77 (3H,m) 7.88 (3H,m) 8.00 (1H,s). MS m/z 625 (M+H)$^+$.

Example 3

A. 1,3-Bis(butyl)-(4α,5α,6β,7β)-hexahydro-5,6-(1-methylethylidene)bis(oxy)-2-phenoxy-4,7-bis(phenylmethyl)-1H-1,3,2-diazaphosphepine 2-oxide.

Using the procedure of Example 1D, but replacing the bromomethylcyclopropane with n-butyl iodide gave the title compound in 50% yield.

B. 1,3-Bis(butyl)-5,6-dihydroxy-(4α,5α,6β,7β)-hexahydro2-phenoxy-4,7-bis(phenylmethyl)-1H-1,3,2-diazaphosphepine 2-oxide.

Using the procedure of Example 1E, but replacing the compound prepared in Example 1D with the compound prepared in Example 3A gave the title compound in 80% yield.

C. (3-endo,4-endo,6-exo)-2,7-Bis(butyl)-3,6-bis(phenylmethyl)-8-oxa-2,7-diaza-1-phosphabicyclo[3.2.1]octan-4-ol 1-oxide.

Using the procedure of Example 1F, but replacing the compound prepared in Example 1E with the compound prepared in Example 3B gave the title compound in 80% yield. Crystallization from methylene chloride/hexane (1/4 v/v) gave prisms, mp 219°–220° C. $^1$H NMR (300 MHz, CDCl$_3$) δ: 0.79 (3H,t) 0.98 (3H,t) 1.05–1.48 (6H,m) 1.64 (1H, d) 1.83 (2H,m) 2.16 (1H,m) 2.65 (1H,dd) 2.82 (1H,dd) 3.00–3.35 (5H,m) 3.50 (1H,m) 3.64 (1H,m) 4.19 (2H,m) 7.26 (10H,m). MS m/z 457 (M+H)$^+$.

Example 4

A. (2R,3S,4S,5R)-2,5-Bis(N-Cbz-amino)-1,6-diphenyl-3,4-bis(O-(trimethylsilylethoxy)methoxy)hexane.

To a suspension of 5 g of (2R,3S,4S,5R)-2,5-bis-(N-Cbz-amino)-3,4-dihydroxy-1,6-diphenylhexane in 25 mL of methylene chloride was added 5.4 mL of diisopropylethylamine followed by 4.7 mL of SEM-Cl. The mixture was stirred at room temperature for 18 hr, followed by dilution with water and extraction with diethyl ether (3X). The combined extracts were quickly and successively washed with 0.1M aqueous hydrochloric acid (1X), water (2X), and saturated sodium chloride solution (1X). After drying over anhydrous sodium sulfate, the organic layer was concentrated by rotary evaporation. Purification of the residue by column chromatography using silica gel eluting with hexane/ethyl acetate (85/15 v/v) gave 5.0 g (68% yield) of the title compound.

B. (2R,3S,4S,5R)-2,5-Diamino-1,6-diphenyl-3,4-bis(O-(trimethylsilylethoxy)methoxy)hexane.

To a solution of 5.0 g of the product prepared in Example 4A in 250 mL of absolute ethanol/cyclohexene (2/1 v/v) was added 1.25 g of Pd(OH)$_2$ (Pearlman's catalyst). The mixture was refluxed for 16 hr with vigorous stirring under a blanket of nitrogen. The catalyst was isolated by filtration through a pad of Celite, and the filtercake washed with ethanol. Concentration of the combined filtrate and washings by rotary evaporation gave 3.2 g (95% yield) of the title compound which was used without further purification in Example 4C.

C. (4α,5α,6β,7β)-Hexahydro-2-phenoxy-4,7-bis(phenylmethyl)-5,6-bis(O-(trimethylsilylethoxy)methyl)-1H-1,3,2-diazaphosphepine 2-oxide.

A solution of 3.2 g of the compound prepared according to the procedure of Example 4B, and 0.55 mL of triethylamine in 9 mL of anhydrous tetrahydrofuran was cooled to 0°–5° C. under a nitrogen atmosphere. With stirring, 0.27 mL of phenyldichlorophosphate in 3 mL of tetrahydrofuran was added dropwise to the cooled solution. The resulting suspension was stirred at room temperature for 1 hr. Triethylamine hydrochloride was isolated by filtration and washed with tetrahydrofuran. The combined filtrate and washings were concentrated by rotary evaporation, taken up in methylene chloride/diethyl ether (1/1 v/v), washed successively with water (2X) and saturated sodium chloride solution (1X), then dried over anhydrous magnesium sulfate. Concentration of the organic layer by rotary evaporation and purification of the residue by column chromatography using silica gel eluting with a hexane/ethyl acetate gradient ranging from 65/35 to 50/50 volume ratios gave 0.97 g (78% yield) of the title compound as a white solid.

D. (4α,5α,6β,7β)-Hexahydro-2-phenoxy-1,3,4,7-tetrakis(phenylmethyl)-5,6-bis(O-(trimethylsilylethoxy)methyl)-1H-1,3,2-diazaphosphepine 2-oxide.

Using the procedure of Example 1D, but replacing the compound prepared in Example 1C with the compound prepared in Example 4C, and replacing the bromomethylcyclopropane with benzyl bromide gave the title compound in 84% yield.

E. (3-endo,4-endo,6-exo)-2,3,6,7-tetrakis (phenylmethyl)-8-oxa-2,7-diaza-1-phosphabicyclo[3.2.1]octan-4-ol 1-oxide.

The compound prepared in Example 4D (0.19 g) was dissolved in 5 mL of 1M tetra-n-butylammonium fluoride in tetrahydrofuran and refluxed overnight in a nitrogen atmosphere. After cooling to room temperature, the mixture was diluted with water and extracted with diethyl ether (3X). Combined extracts were dried over sodium sulfate, filtered, and the solvent was removed in vacuo. Column chromatography on silica gel eluting with hexane/ethyl acetate (65/35 v/v) gave a low yield of the title compound as a white solid. mp 82°–83° C. $^1$H NMR (300 MHz, CDCl$_3$) δ: 1.44 (1H,d) 2.49–3.78 (3H,m) 3.04 (1H,m) 3.19 (1H,dd) 3.46 (1H,m) 3.78 (2H,m) 4.17 (2H,m) 4.57 (1H,dd) 4.84 (1H,dd) 7.05 (2H,dd) 7.24 (6H,m) 7.40 (2H,t) 7.64 (2H,d). MS m/z 525 (M+H)$^+$.

Example 5

A. (4α,5α,6β,7β)-Hexahydro-5,6-(1-methylethylidene)bis(oxy)-2-phenoxy-4,7-bis(phenylmethyl)-1,3-bis(4-(tetrahydropyranyloxymethyl)phenylmethyl)-1H-1,3,2-diazaphosphepine 2-oxide.

Using the procedure of Example 1D, but replacing the bromomethylcyclopropane with 4-(tetrahydropyranyloxymethyl)benzyl chloride gave the title compound in 71% yield.

B. 5,6-Dihydroxy-(4α,5α,6β,7β)-hexahydro-1,3-bis(4-(hydroxymethyl)phenylmethyl)-2-phenoxy-4,7-bis(phenylmethyl)-1H-1,3,2-diazaphosphepine 2-oxide.

To a solution of 0.12 g of the compound prepared in Example 5A in 3 mL of methanol was added 0.01 g p-toluenesulfonic acid monohydrate. The solution was stirred for 1 hr at room temperature, then concentrated by rotary evaporation. The residue was taken up in ethyl acetate, washed with saturated sodium hydrogen carbonate solution, and dried over anhydrous magnesium sulfate. Concentration by rotary evaporation and purification by column chromatography on silica gel using methylene chloride/ethyl acetate/ethanol (10/10/0.5 volume ratios) gave 54 mg (59% yield) of the title compound.

C. (3-endo,4-endo,6-exo)-2,7-Bis(4-(hydroxymethyl)phenylmethyl)-3,6-bis(phenylmethyl)-8-oxa-2,7-diaza-1-phosphabicyclo[3.2.1]octan-4-ol 1-oxide To a solution of 0.63 g of the compound prepared in Example 5B in 20 mL of tetrahydrofuran/water (3/1 v/v) was added 1.95 mL of 1M aqueous lithium hydroxide. After stirring for 1 hr at room temperature, the mixture was diluted with water and extracted with diethyl ether (3X). The combined extracts were washed with saturated sodium chloride solution, dried over anhydrous magnesium sulfate, and concentrated by rotary evaporation. Purification of the residue by column chromatography using silica gel eluting with methylene chloride/ethyl acetate (1/1 v/v) followed by methylene chloride/ethyl acetate/ethyl alcohol (10/10/0.5) gave 0.42 g (77%) of the title compound, mp 107°–110° C. $^1$H NMR (300 MHz, DMSO-d$_6$) δ: 2.37 (1H,dd) 2.59 (2H,m) 2.80 (1H,t) 3.21 (2H,m) 3.58 (1H,m) 3.76 (1H,m) 4.04 (1H,dd) 4.29 (1H,dd) 4.47 (5H,m) 4.61 (1H,dd) 5.11 (2H,m) 5.35 (1H,d) 6.96 (2H,d) 7.11–7.39 (14H,m) 7.62 (2H,d). MS m/z 585 (M+H)$^+$.

Example 6

A. (4α,5α,6β,7β)-Hexahydro-5,6-(1-methylethylidene)bis(oxy)-1,3-bis(3-(N-methyl, N-trifluoroacetamido)phenylmethyl)-2-phenoxy-4,7-bis(phenylmethyl)-1H-1,3,2-diazaphosphepine 2-oxide.

Using the procedure of Example 1D but replacing the bromomethylcyclopropane with 3-(N-methyl,N-trifluoroacetamido)benzyl bromide gave the title compound in 96% yield.

B. (4α,5α,6β,7β)-Hexahydro-1,3-bis(3-(methylamino)phenylmethyl)-5,6-(1-methylethylidene)bis(oxy)-2-phenoxy-4,7-bis(phenylmethyl)-1H-1,3,2-diazaphosphepine 2-oxide.

A solution of 0.27 g of the compound prepared in Example 6A in 7 mL of methanol was treated with 4 eq of solid potassium carbonate. The mixture was stirred for 48 hr at room temperature, diluted with water, and extracted with methylene chloride. The extract was washed successively with saturated sodium hydrogen carbonate solution and saturated sodium chloride solution, then dried over anhydrous magnesium sulfate. Concentration by rotary evaporation and purification of the residue by column chromatography using silica gel eluting with hexane/ethyl acetate (1/1 v/v) gave the title compound in 57% yield.

C. 5,6-Dihydroxy-(4α,5α,6β,7β)-hexahydro-1,3-bis(3-(methylamino)phenylmethyl)-2-phenoxy-4,7-bis(phenylmethyl)-1H-1,3,2-diazaphosphepine 2-oxide.

Using the procedure of Example 5B, but replacing the compound prepared in Example 5A with the compound prepared in Example 6B gave the title compound in 19% yield.

D. (3-endo,4-endo,6-exo)-2,7-Bis(3-(methylamino)phenylmethyl)-3,6-bis(phenylmethyl)-8-oxa-2,7-diaza-1-phosphabicyclo[3.2.1]octan-4-ol 1-oxide.

Using the procedure of Example 1F, but replacing the compound prepared in Example 1E with the compound prepared in Example 6C gave the title compound in 10% yield. $^1$H NMR (300 MHz, CDCl$_3$) δ: 2.01 (2H,m) 2.35 (1H,t) 2.54–2.70 (2H,m) 2.79 (3H,s) 2.84 (1H,d) 2.87 (3H,s) 3.01 (1H,t) 3.17 (1H,dd) 3.50 (1H,m) 3.70 (1H,m) 3.88 (1H,dd) 4.13 (2H,m) 4.50 (1H,dd) 4.72 (1H,dd) 6.45 (2H,d) 6.54 (1H,dd) 6.89 (1H,d) 6.95 (1H,s) 7.06 (2H,d) 7.13–7.33 (11H,m). MS m/z 583 (M+H)$^+$.

Example 7

A. (4α,5α,6β,7β)-hexahydro-5,6-(1-methylethylidene)bis(oxy)-2-phenoxy-1,3-Bis(4-(phenylmethoxy)phenylmethyl)-4,7-bis(phenylmethyl)-1H-1,3,2-diazaphosphepine 2-oxide.

Using the procedure of Example 1D, but replacing the bromomethylcyclopropane with 4-(phenylmethoxy)benzyl chloride gave the title compound in 55% yield.

B. 1,3-Bis(4-hydroxyphenylmethyl)-(4α,5α,6β,7β)-hexahydro-5,6-(1-methylethylidene)bis(oxy)-2-phenoxy-4,7-bis(phenylmethyl)-1H-1,3,2-diazaphosphepine 2-oxide.

A solution of 80 mg of the compound prepared in Example 7A in 15 mL of ethanol/cyclohexene (2/1 v/v) was treated with 40 mg of Pd(OH)$_2$ (Pearlman's catalyst). The mixture was refluxed under a nitrogen atmosphere for 4.5 hr. Catalyst was removed by filtration and washed with ethanol and ethyl acetate. Concentration of the combined filtrate and washings by rotary evaporation gave the title compound in 66% yield, which was used in Example 7C without further purification.

C. 5,6-Dihydroxy-(4α,5α,6β,7β)-hexahydro-1,3-bis(4-hydroxyphenylmethyl)-2-phenoxy-4,7-bis(phenylmethyl)-1H-1,3,2-diazaphosphepine 2-oxide.

Using the procedure of Example 5B, but replacing the compound prepared in Example 5A with the compound prepared in Example 7B gave the title compound in 45% yield.

D. (3-endo,4-endo,6-exo)-2,7-bis(4-hydroxyphenylmethyl)-3,6-bis(phenylmethyl)-8-oxa-2,7-diaza-1-phosphabicyclo[3.2.1]octan-4-ol 1-oxide.

Using the procedure of Example 1F, but replacing the compound prepared in Example 1E with the compound prepared in Example 7C gave the title compound in 83% yield, mp 134°–135° C. $^1$H NMR (300 MHz, acetone-d$_6$) δ: 2.44 (1H,dd) 2.70 (1H,dd) 2.80 (1H,m) 3.34 (1H,m) 3.47 (1H,m) 3.75 (1H,m) 3.87 (1H,m) 4.15 (1H,dd) 4.30–4.48 (3H,m) 4.71 (1H,dd) 6.74 (2H,d) 6.88 (2H,d) 6.95 (2H,d) 7.15 (3H,m) 7.24 (3H,m) 7.38 (4H,d) 7.59 (2H,d) 8.29 (1H,s) 8.33 (1H,s). MS m/z 557 (M+H)$^+$.

Example 8

A. (4α,5α,6β,7β)-hexahydro-5,6-(1-methylethylidene)bis-(oxy)-1,3-bis(3-(tetrahydropyranyloxymethyl)phenylmethyl)-2-phenoxy-4,7-bis(phenylmethyl)-1H-1,3,2-diazaphosphepine 2-oxide.

Using the procedure of Example 1D, but replacing the bromomethylcyclopropane with 3-(tetrahydropyranyloxymethyl)benzyl chloride gave the title compound in 72% yield.

B. 5,6-Dihydroxy-(4α,5α,6β,7β)-hexahydro-1,3-bis(3-(hydroxymethyl)phenylmethyl)-2-phenoxy-4,7-bis(phenylmethyl)-1H-1,3,2-diazaphosphepine 2-oxide.

Using the procedure of Example 5B, but replacing the compound prepared in Example 5A with the compound prepared in Example 8A gave the title compound in 50% yield.

C. (3-endo,4-endo,6-exo)-2,7-Bis(3-(hydroxymethyl)phenylmethyl)-3,6-bis(phenylmethyl)-8-oxa-2,7-diaza-1-phosphabicyclo[3.2.1]octan-4-ol 1-oxide Using the procedure of Example 1F, but replacing the compound prepared in Example 1E with the compound prepared in Example 8B gave the title compound in 33% yield. $^1$H NMR (300 MHz, acetone-d$_6$) δ: 2.29 (1H,dd) 3.02 (1H,t) 3.37 (1H,dd) 3.47 (1H,m) 3.86 (1H,m) 3.92 (1H,m) 4.19 (2H,m) 4.28 (1H,t) 4.40–4.52 (3H,m) 4.58 (2H,d) 4.68 (2H,d) 4.79 (1H,dd) 7.02 (1H,m) 7.10–7.40 (15H,m) 7.66 (1H,d) 7.73 (1H,s). MS m/z 585 (M+H)$^+$, 602 (M+NH4)$^+$.

UTILITY

The compounds of formula (I) possess retroviral protease inhibitory activity and are therefore useful as antiviral agents for the treatment of viral diseases. More particularly, the compounds of formula (I) possess HIV protease inhibitory activity and are effective as inhibitors of HIV growth. The protease inhibitory activity of the compounds of the present invention is demonstrated using standard assays of protease activity, as shown, for example, using the assays described below for assaying inhibitors of HIV protease activity. The ability of the compounds of the present invention to inhibit viral growth or infectivity is demonstrated in a standard assay of viral growth or infectivity, as shown, for example, using the assays described below.

The compounds provided by this invention are also useful as standards and reagents in determining the ability of a potential pharmaceutical to inhibit viral replication of HIV protease. These would be provided in commercial kits comprising a compound of this invention.

As used herein "ug" denotes microgram, "mg" denotes milligram, "g" denotes gram, "uL" denotes microliter, "mL" denotes milliliter, "L" denotes liter, "nM" denotes nanomolar, "uM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an IC$_{50}$ or Ki value of less than about 1 mM for the inhibition of HIV protease or HIV viral growth or infectivity.

HIV PROTEASE INHIBITION ASSAY
(SPECTROSCOPIC METHOD)

Materials

Protease: Inclusion bodies of E. coli harboring plasmid containing HIV protease under the control of an inducible T7 promoter were prepared according to Cheng et al. *Gene* 1990, 87, 243. Inclusion bodies were solubilized in 8M urea, 50 mM tris, pH 8.0. Protease activity was recovered by dilution 20-fold into buffer containing 50 mM sodium acetate, pH 5.5, 1 mM EDTA, 10% glycerol and 5% ethylene glycol. Enzyme was used at a final concentration of 1.0–10.0 ug/mL.

Substrate: Peptide of the sequence Ala-Thr-His-Gln-Val-Tyr-Phe($NO_2$)-Val-Arg-Lys-Ala, containing p-nitrophenylalanine (Phe($NO_2$)), was prepared by solid phase peptide synthesis as previously described by Cheng et al. *Proc. Natl. Acad. Sci. USA* 1990, 87, 9660. Stock solutions of 10 mM were prepared in DMSO. Inhibitor compounds were dissolved in sufficient DMSO to make 2.5 or 25 mM stock solutions. All further dilutions were done in DMSO.

Reactions

Compound (1–5 uL) and HIV protease were mixed in buffer containing 50 mM MES (2-(N-morpholino)ethane sulfonic acid), pH 5.5, 1M NaCl, 1 mM EDTA, 1 mM dithiothreitol and 10% glycerol. Reactions were initiated by the addition of peptide substrate to a final concentration of 240 uM, and absorbance at 300 nm was monitored for 10 min. Values of Ki for inhibitor binding were determined from percent activity measurements in the presence and absence of known concentration of inhibitor, using a value of 0.07 mM for the Km of the substrate (Cheng et al. *Proc. Natl. Acad. Sci. USA* 1990, 87, 9660).

The HIV-1 protease inhibitory activity of representative compounds of the invention is shown in TABLE 1. The Ki values in TABLE 1 were determined using the assay conditions described below under HIV Protease Inhibition Assay (HPLC Method). The Ki values are indicated as follows: +++=<10 nM; ++=10 nM to 1 µM; +=>1 mM.

TABLE 1

| HIV Protease Inhibition Data | |
|---|---|
| Example No. | $K_i$ |
| 1F | ++ |
| 2C | ++ |
| 3C | ++ |
| 4E | ++ |
| 5C | +++ |
| 6D | ++ |
| 7D | +++ |
| 8C | +++ |

HIV PROTEASE INHIBITION ASSAY (HPLC METHOD)

Materials

Protease: Inclusion bodies of E. coli harboring plasmid T1718R with a synthetic gene coding for a single-chain tethered dimer of HIV protease were prepared as described in Cheng et al. *Proc. Natl. Acad. Sci. USA* 1990, 87, 9660. Active protease was prepared as described therein by extraction with 67% acetic acid, dilution 33-fold with water, dialysis against water and then against a "refolding buffer" comprising 20 mM MES, 1 mM dithiothreitol and 10% glycerol, pH 5.5. Protease was stored as a stock preparation at 10 uM in refolding buffer.

Substrate: Peptide of the sequence aminobenzoyl-Ala-Thr-His-Gln-Val-Tyr-Phe($NO_2$)-Val-Arg-Lys-Ala containing p-nitrophenylalanine (Phe($NO_2$)), was prepared by solid phase synthesis as previously described (Cheng et al. *Proc. Natl. Acad. Sci. USA* 1990, 87, 9660). Stock solutions of 2 mM substrate were prepared in DMSO.

Inhibitory compounds were dissolved in sufficient DMSO to make 3 mM stock solutions. All further dilutions were prepared in "assay buffer" comprising 1M NaCl, 50 mM MES, pH 5.5, 1 mM EDTA, 1 mM DTT and 20% glycerol.

Reactions

Enzyme reaction: To a 2 mL screw-cap centrifuge tube were added 50 uL protease (final concentration 0.25 nM) and 0.1 mL inhibitor compound (final concentration 0.1–12,500 nM). After 15 min preincubation at room temperature, the reaction was started by the addition of 0.05 mL substrate (final concentration 5 uM). Incubation was carried out at 30° C. for 1 hr. The reaction was stopped by addition of 1 mL of 0.1M ammonium hydroxide solution.

HPLC measurement of product formation: The product (aminobenzoyl-Ala-Thr-His-Gln-Val-Tyr) was separated from substrate on a Pharmacia MonoQ anion exchange column. The injection volume was 0.2 mL. The mobile phases comprised: solution A (20 mM tris HCl, pH 9.0, 0.02% sodium azide, 10% acetonitrile), and solution B (20 mM tris HCl, pH 9.0, 0.02% sodium azide, 0.5M ammonium formate, 10% acetonitrile). The mobile phases were pumped at 1 mL/min, with a gradient from 0 to 30% B in 5 min, 100% B for 4 min to wash the column, and a re-equilibration wash with A for 4 min. The retention time of the product was 3.6 min. Detection with a Shimadzu model RF535 fluorescence monitor was at 330 nm (excitation) and 430 nm (emission). The Ki was calculated from the formula $Ki=I/(((Km+S-FA*S)/(FA*Km))-1)$ where I=inhibitor concentration, S=substrate concentration, FA=fractional activity=cm peak height with inhibitor/cm peak height without inhibitor and Km=Michaelis constant=20 uM.

HIV YIELD REDUCTION CELL ASSAY

The following procedure is additionally described in Smallheer et al. *Antiviral Chemistry and Chemotherapy* 1993, 4(1), 27.

Materials

MT-$_2$, a human T-cell line, was cultured in RPMI medium supplemented with 5% (v/v) heat inactivated fetal calf serum (FCS), 2 mM L-glutamine and 50 µg/mL gentamycin (later two compounds available from Gibco) Human immunodeficiency virus strains, HIV (3B) and HIV (RF) were propagated in H-9 cells in RPMI with 5% FCS. Poly-L-lysine (Sigma) coated cell culture plates were prepared according to the method of Harada et al. *Science* 1985, 229 563. MTT, (3-(4,5-dimethyl-thiazol-2-yl)- 2,5-diphenyltetrazolium bromide), was obtained from Sigma.

Method: Test compounds were dissolved in dimethylsulfoxide to 5 mg/mL and serially diluted into RPMI medium to ten times the desired final concentration. MT-2 cells ($5\times10^5$/mL) in 2.3 mL RPMI solution were mixed with 0.3 mL of the appropriate test compound solution and allowed to sit for 30 minutes at room temperature. HIV (3B) or HIV (RF) (~$5\times10^5$ plaque forming units/mL) in 0.375 mL was added to the cell/compound mixtures and incubated for one hour at 36° C. The mixtures were centrifuged at 1000 rpm for 10 minutes and the supernatants containing unattached virus were discarded. The cell pellets were suspended in fresh RPMI containing the appropriate concentrations of test compound and placed in a 36° C., 4% $CO_2$ atmosphere incubator. Virus was allowed to replicate for 3 days. Cultures were centrifuged for 10 minutes at 1000 rpm and the supernatants containing cell free progeny virus were removed for plaque assay.

The virus titers of the progeny virus produced in the presence or absence of test compounds were determined by plaque assay. Progeny virus suspensions were serially diluted in RPMI and 1.0 mL of each dilution was added to 9 mL of MT-2 cells in RPMI. Cells and virus were incubated for 3 hours at 36° C. to allow for efficient attachment of the virus to the cells. Each virus and cell mixture was aliquoted equally to two wells of a six well poly-L-lysine coated culture plate and incubated overnight at 36° C., 4% $CO_2$ atmosphere. Liquid and unattached cells were removed prior to the addition of 1.5 mL of RPMI containing 0.75% (w/v) Seaplaque agarose (FMC Corp.) and 5% FCS. Plates were incubated for 3 days and then a second RPMI/agarose overlay was added. After an additional 3 days at 36° C. in an atmosphere containing 4% $CO_2$, a final overlay of phosphate-buffered saline containing 0.75% Seaplaque agarose and 1 mg MTT/mL was added. The plates were incubated overnight at 36° C. Clear plaques on a purple background were counted and the number of plaque forming units of virus was calculated for each sample. The antiviral activity of test compounds was determined by the percent reduction in the virus titer with respect to virus grown in the absence of inhibitor. The $IC_{90}$ values in TABLE 2 were determined using the assay conditions described above under HIV Yield Reduction Assay. The $IC_{90}$ values are indicated as follows: +++=<10 µg/mL; ++=10 to 100 µg/mL; +=>100 µg/mL.

TABLE 2

| HIV Yield Reduction Data | |
|---|---|
| Example No. | $IC_{90}$ |
| 5C | +++ |

HIV RNA ASSAY

DNA Plasmids and In Vitro RNA Transcripts

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotinphosphoramidite reagent of Cocuzza, *Tet. Lett.* 1989, 30, 6287. The gag biotinylated capture probe (5-biotin-CTAGCTCCCTGCT-TGCCCATACTA 3') was complementary to nucleotides 889–912 of HXB2 and the pol biotinylated capture probe (5'-biotin —CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCT-TACTTTGATAAAACCTC 3') was complementary to nucleotides 2403–2425 of HXB2. The gag reporter probe (5' CCCAGTATTTGTCTACAGCCTTCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 µM stocks in 2×SSC(0.3M NaCl, 0.03M sodium citrate), 0.05M Tris pH 8.8, 1 mg/mL BSA. The biotinylated capture probes were prepared as 100 µM stocks in water.

Streptavidin Coated Plates

Nunc-immunomodule microtiter plate strips were coated by addition of 200 µL of streptavidin (30 µg/mL, Scripps, La Jolla, Calif.) in freshly prepared 10 mM sodium carbonate (pH 9.6). Plates were incubated overnight at 4° C. Streptavidin solution was aspirated from the wells and a blocking buffer composed of phosphate buffered saline (PBS), 20 mg/mL bovine serum albumin (crystalline, nuclease and protease free, Calbiochem) and 100 mg/mL lactose (Sigma) was added to the plates for 3 hrs at room temperature. Blocking buffer was removed from the wells, which were allowed to dry overnight at room temperature and subsequently stored at 4° C. in zip lock bags with desiccant. For the majority of the compound evaluation experiments, streptavidin coated plates were obtained from Du Pont Biotechnology Systems (Boston, Mass.).

Cells and Virus Stocks $MT_{-2}$, CEM, and H9 cells were maintained in RPMI 1640 supplemented with 5% fetal calf serum (FCS), 2 mM L-glutamine and 50 µg/mL gentamycin, all from Gibco. Laboratory strains of HIV-1 (RF, MN and IIIB) were propagated in H9 cells in the same medium. Virus stocks were prepared approximately 1 month after acute infection of H9 cells by clarification of the tissue culture medium and storage of aliquots at −70° C. Infectious titers of HIV-1 (RF) stocks were $1-3\times10^7$ PFU (plaque forming units)/mL as measured by plaque assay on MT-2 cells (see below). Each aliquot of virus stock used for infection was thawed only once. In some cases, infected H9 cells were shifted to Dulbecco's modified Eagle's medium 3–10 days before collection of virus in order to generate virus stocks in medium with low biotin content. Clinical isolates of HIV that had been passaged once in MT-2 cells were used to infect fresh MT-2 cells in RPMI medium. Three days after infection, cells were pelleted, resuspended and culture continued in Dulbecco's modified Eagle's medium as above. Virus stocks of clinical isolates were prepared 10–15 days after infection when cytopathic effects were apparent in the culture.

For evaluation of antiviral efficacy, cells to be infected were subcultured one day prior to infection. On the day of infection, cells were resuspended at $5\times10^5$ cells/mL in RPMI 1640, 5% FCS for bulk infections or at $2\times10^6$/mL in either Dulbecco's modified Eagles medium, or RPMI 1640 medium minus biotin (Gibco, custom formulation) with 5% FCS for infection in microtiter plates. Virus was added and culture continued for 3 days at 37° C. In some experiments, virus was removed after an initial adsorption period.

Preparation of HIV-1 Infected Cell Lysates

HIV-1 infected cells were pelleted by centrifugation. After removal of the supernatant the cells were resuspended at a concentration of $1\times10^7$ cells/mL in 5M guanidinium isothiocyanate solution (GED: 5M guanidinium isothiocyanate (Sigma), 0.1M EDTA, 10% dextran sulfate). Alternately, cells grown in biotin free tissue culture medium were mixed with 5M GED to a final concentration of 3M guanidinium isothiocyanate, 0.06M EDTA and 6% dextran sulfate.

HIV RNA Assay

Cell lysates or purified RNA in 3M or 5M GED were mixed with 5M GED and capture probe to a final guanidinium isothiocyanate concentration of 3M and a final biotin oligonucleotide concentration of 30 nM. Hybridization was carried out in sealed microfuge tubes or in sealed U bottom 96 well tissue culture plates (Nunc or Costar) for 16–20 hours at 37° C. RNA hybridization reactions were diluted three-fold with deionized water to a final guanidinium isothiocyanate concentration of 1M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline (PBS), 0.05% Tween 20.) A second hybridization of reporter probe to the immobilized complex of capture probe and hybridized target RNA was carried out in the washed streptavidin coated well by addition of 120 µl of a hybridization cocktail containing 4×SSC, 0.66% Triton×100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer D (2.5M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2Cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of $5\times10^5$ per mL ($1\times10^5$ per well). Cells were incubated with compounds for 30 minutes at 37° C. in a $CO_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 µL of medium/well was removed from the HIV infected plates. Thirty seven µL of 5M GED containing biotinylated capture probe was added to the settled cells and remaining medium in each well to a final concentration of 3M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 µg/mL. $IC_{90}$ values of other antiviral compounds, both more and less potent than ddC, were reproducible using several stocks of HIV-1 (RF) when this procedure was followed. This concentration of virus corresponded to $\sim 3\times10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 µg/mL. Finally, the plateau level of viral RNA produced by an effective protease inhibitor should be less than 10% of the level achieved in an uninhibited infection.

For antiviral potency tests, all manipulations in microtiter plates, following the initial addition of 2X concentrated compound solution to a single row of wells, were performed using a Perkin Elmer/Cetus ProPette.

The HIV inhibitory activity of representative compounds of the present invention in the RNA assay described above is shown in TABLE 3. The $IC_{90}$ values in TABLE 3 were determined using the assay conditions described above under HIV RNA Assay. The $IC_{90}$ values are indicated as follows: +++=<10 ug/mL; ++=10 to 100 ug/mL; +=>100 ug/mL. The ++/+ is used in the cases where an $IC_{90}$ was determined to be >50 ug/mL.

TABLE 3

| Antiviral Data | |
|---|---|
| Example No. | $IC_{90}$ |
| 1F | ++ |
| 2C | ++/+ |
| 3C | ++/+ |
| 4E | ++ |
| 5C | +++ |
| 6D | +++ |
| 7D | +++ |
| 8C | +++ |

DOSAGE AND FORMULATION

The antiviral compounds of this invention can be administered as treatment for viral infections by any means that produces contact of the active agent with the agent's site of action, i.e., the viral protease, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol.

Suitable pharmaceutical carriers are described in *Remington's Pharmaceutical Sciences,* supra, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 100 mg of powdered active ingredient, 150 mg of lactose, 50 mg of cellulose, and 6 mg magnesium stearic.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 mg of the active ingredient. The capsules are washed and dried.

TABLETS

A large number of tablets were prepared by conventional procedures so that the dosage unit was 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

I claim:

1. A compound of formula (Ia):

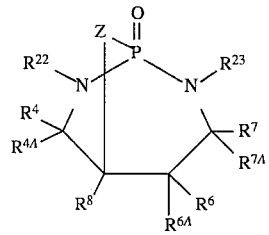

or pharmaceutically acceptable salt or prodrug form thereof wherein:

Z is O;

each of $R^4$ and $R^7$ is independently:
hydrogen, —O($R^{13}$), —S($R^{13}$), —C(=O)O($R^{13}$), $C_1$-$C_8$ alkyl substituted with 0–3 $R^{11}$, $C_2$-$C_8$ alkenyl substituted with 0–3 $R^{11}$, $C_2$-$C_8$ alkynyl substituted with 0–3 $R^{11}$, a $C_3$-$C_{14}$ carbocyclic ring system substituted with 0–3 $R^{11}$ or 0–3 $R^{12}$, or a 5- to 10-membered heterocyclic ring system containing 1 to 4 heteroatoms independently selected from oxygen, nitrogen or sulfur, the heterocyclic ring system being substituted with 0–2 $R^{12}$;

each of $R^{4A}$ and $R^{7A}$ is independently:
hydrogen, —O($R^{13}$), —S($R^{13}$), —C(=O)O($R^{13}$), $C_1$-$C_4$ alkyl unsubstituted or substituted with halogen or $C_1$-$C_2$ alkoxy, or phenylmethyl unsubstituted or substituted with halogen or $C_1$-$C_2$ alkoxy;

each of $R^6$ and $R^{6A}$ is independently:
hydrogen, halogen, —N($R^{20}$)$_2$, —S($R^{20}$), —O($R^{21}$) or $C_1$-$C_6$ alkyl substituted with 0–3 $R^{11}$;

$R^6$ and $R^{6A}$ can alternatively join to form =O, =S or a ketal ring;

$R^8$ is: hydrogen, $C_1$-$C_3$ alkyl or $C_1$-$C_3$ perfluoroalkyl;

$R^8$ can alternatively join with any of $R^6$ or $R^{6A}$ to form
—OCH$_2$SCH$_2$O—, —OS(=O)O—, —OC(=O)O—,
—OCH$_2$)—, —OC(=S)O—, —OC(=O)C(=O)—,
—OC(CH$_3$)$_2$O—, —OC((CH$_2$)$_3$NH$_2$) (CH$_3$)O—,
—OC(OCH$_3$) (CH$_2$CH$_2$CH$_3$)O—, —OS(=O)$_2$O—,
—NHC(=O)NH—, —OC(=O)NH—,
—NHC(=O)O—, —NHCH$_2$O—, —OCH$_2$NH—,
—NHC(=S)O—, —OC(=S)NH—,
—OS(=O)NH—, —NHS(=O)O—, —NHC(=O)C(=O)O—, —OC(=O)C(=O)NH—, —NHC(=O)C(=O)NH—, —NHC(CH$_3$)$_2$O—, —OC(CH$_3$)$_2$NH— or any group that, when administered to a mammalian subject as part of a compound of formula (I), cleaves to form a compound having two free hydroxyl groups, or two free amino groups, or one free hydroxyl and one free amino group;

each $R^{11}$ is independently:
   hydrogen, keto, halogen, phenylmethyl, phenethyl, methylenedioxy, ethylenedioxy, hydroxamic acid, hydrazide, boronic acid, sulfonamide, azido, formyl, phenoxy, phenylmethoxy, nitro, cyano, —CH$_2$N(R$^{13}$) (R$^{14}$), —N(R$^{13}$) (R$^{14}$), —OCH$_2$C(=O)OH, —C(=O)O(R$^{13}$), —OC(=O)(R$^{13}$), —O(R$^{13}$), C$_2$-C$_6$ alkoxyalkyl, —S(=O)$_m$(R$^{13}$), —NHC(=NH)NH(R$^{13}$), —C(=NH)NH(R$^{13}$), —C(=O)N(R$^{13}$) (R$^{14}$), —N(R$^{14}$)C(=O) (R$^{13}$), =N—O(R$^{14}$), —N(R$^{14}$)C(=O)O(R$^{14}$), —OC(=O)N(R$^{13}$) (R$^{14}$), —N(R$^{13}$)C(=O)N(R$^{13}$) (R$^{14}$), —C(R$^{14}$)=N—O(R$^{14}$), —N(R$^{14}$)S(=O)$_2$N(R$^{13}$) (R$^{14}$), —N(R$^{14}$)S(=O)$_2$ (R$^{13}$), —S(=O)$_2$N(R$^{13}$) (R$^{14}$), C$_1$-C$_4$ alkyl, C$_2$-C$_4$ alkenyl, C$_3$-C$_{10}$ cycloalkyl, C$_3$-C$_6$ cycloalkylmethyl, C$_7$-C$_{10}$ arylalkyl, C$_3$-C$_6$ cycloalkoxy, C$_1$-C$_4$ alkyl substituted with —N(R$^{13}$) (R$^{14}$), C$_1$-C$_4$ hydroxyalkyl, C$_1$-C$_4$ haloalkyl, C$_1$-C$_4$ haloalkoxy, C$_1$-C$_4$ alkoxycarbonyl, C$_1$-C$_4$ alkylcarbonyloxy, C$_1$-C$_4$ alkylcarbonyl, C$_1$-C$_4$ alkylcarbonylamino, 2-(1-morpholino)ethoxy, —(C$_1$-C$_3$ alkyl)aryl substituted with 0-2 R$^{12}$,
   a C$_5$-C$_{14}$ carbocyclic residue substituted with 0-3 R$^{12}$, or
   a 5- to 10-membered heterocyclic ring system containing 1 to 4 heteroatoms independently selected from oxygen, nitrogen or sulfur, the heterocyclic ring system being substituted with 0-3 R$^{12}$;

m is: 0, 1 or 2;

each $R^{114}$ is independently:
   H, keto, halogen, cyano, —CH$_2$NH$_2$, —NH$_2$, —CO$_2$H, —OC(=O)(C$_1$-C$_3$ alkyl), —OH, C$_2$-C$_6$ alkoxyalkyl, —C(=O)NH$_2$, —OC(=O)NH$_2$, —NHC(=O)NH$_2$, —S(=O)$_2$NH$_2$, C$_1$-C$_4$ alkyl, C$_2$-C$_4$ alkenyl, C$_3$-C$_{10}$ cycloalkyl, C$_3$-C$_6$ cycloalkylmethyl, benzyl, phenethyl, phenoxy, benzyloxy, nitro, C$_7$-C$_{10}$ arylalkyl, hydroxamic acid, hydrazide, boronic acid, C$_3$-C$_6$ cycloalkoxy, C$_1$-C$_4$ alkyl substituted with —NH$_2$, C$_1$-C$_4$ hydroxyalkyl, methylenedioxy, ethylenedioxy, C$_1$-C$_4$ haloalkyl, C$_1$-C$_4$ haloalkoxy, C$_1$-C$_4$ alkoxycarbonyl, C$_1$-C$_4$ alkylcarbonyloxy, C$_1$-C$_4$ alkylcarbonyl, C$_1$-C$_4$ alkylcarbonylamino, —OCH$_2$C(=O)OH, 2-(1-morpholino)ethoxy, azido, aryl(C$_1$-C$_3$ alkyl), a C$_5$-C$_{14}$ carbocyclic residue, or a 5- to 10-membered heterocyclic ring system containing 1 to 4 heteroatoms independently selected from oxygen, nitrogen or sulfur;

each $R^{12}$ when a substituent on carbon, is independently:
   phenyl, phenylmethyl, phenethyl, phenoxy, phenylmethoxy, halogen, hydroxy, nitro, cyano, C$_1$-C$_4$ alkyl, C$_3$-C$_6$ cycloalkyl, C$_3$-C$_6$ cycloalkylmethyl, C$_7$-C$_{10}$ arylalkyl, C$_1$-C$_4$ alkoxy, —C(=O)OH, hydroxamic acid, hydrazide, boronic acid, sulfonamide, formyl, C$_3$-C$_6$ cycloalkoxy, —O(R$^{13}$), C$_1$-C$_4$ alkyl substituted with —N(R$^{13}$) (R$^{14}$), —N(R$^{13}$) (R$^{14}$), C$_2$-C$_6$ alkoxyalkyl, C$_1$-C$_4$ hydroxyalkyl, methylenedioxy, ethylenedioxy, C$_1$-C$_4$ haloalkyl, C$_1$-C$_4$ haloalkoxy, C$_1$-C$_4$ alkoxycarbonyl, C$_1$-C$_4$ alkylcarbonyloxy, C$_1$-C$_4$ alkylcarbonylamino, —S(=O)$_m$(R$^{13}$), —S(=O)$_2$N(R$^{13}$) (R$^{14}$), —NHS(=O)$_2$(R$^{14}$), —OCH$_2$C(=O)OH, 2-(1-morpholino)ethoxy, —C(R$^{14}$)=N—O(R$^{14}$),
   a 5- to 10-membered heterocyclic ring containing from 1 to 4 heteroatoms independently selected from oxygen, nitrogen or sulfur, the heterocyclic ring system being substituted with 0-3 R$^{15}$,
   a 3- or 4-carbon chain attached to an adjacent carbon on the ring to which it is appended to form a fused 5- or 6-membered ring, the 5- or 6-membered ring being optionally substituted on any of the aliphatic carbons with halogen, C$_1$-C$_4$ alkyl, C$_1$-C$_4$ alkoxy, hydroxy, —N (R$^{13}$) (R$^{14}$), or
   when $R^{12}$ is attached to a saturated carbon atom, $R^{12}$ may be =O or =S;

each $R^{12}$, when a substituent on nitrogen, is independently: phenyl, phenylmethyl, phenethyl, hydroxy, C$_1$-C$_4$ hydroxyalkyl, C$_1$-C$_4$ alkoxy, C$_1$-C$_4$ alkyl, C$_3$-C$_6$ cycloalkyl, C$_3$-C$_6$ cycloalkylmethyl, —CH$_2$N(R$^{13}$) (R$^{14}$), —N(R13) (R$^{14}$), C2-C$_6$ alkoxyalkyl, C$_1$-C$_4$ haloalkyl, C$_1$-C$_4$ alkoxycarbonyl, —C(=O) OH, C$_1$-C$_4$ alkylcarbonyloxy, C$_1$-C$_4$ alkylcarbonyl or —C(R$^{14}$)=N—O(R$^{14}$);

each $R^{13}$ is independently:
   hydrogen, phenyl substituted with 0-3 R$^{11A}$, phenylmethyl substituted with 0-3 R$^{11A}$, C$_1$-C$_6$ alkyl substituted with 0-3 R$^{11A}$, C$_2$-C$_4$ alkenyl substituted with 0-3 R$^{11A}$, C$_1$-C$_6$ alkylcarbonyl substituted with 0-3 R$^{11A}$, C$_1$-C$_6$ alkoxycarbonyl substituted with 0-3 R$^{11A}$, C$_1$-C$_6$ alkylaminocarbonyl substituted with 0-3 R$^{11A}$, C$_3$-C$_6$ alkoxyalkyl substituted with 0-3 R$^{11A}$, an amine protecting group when $R^{13}$ is bonded to N, or a hydroxy protecting group when $R^{13}$ is bonded to O;

each $R^{14}$ is independently:
   hydrogen, hydroxy, trifluoromethyl, C$_1$-C$_6$ alkoxy, C$_2$-C$_6$ alkenyl, phenylmethyl, amino,
   C$_1$-C$_6$ alkyl substituted with 0-3 groups selected from hydroxy, C$_1$-C$_4$ alkoxy, halogen, amino,
   an amine protecting group when $R^{14}$ is bonded to N, or a hydroxy protecting group when $R^{14}$ is bonded to O;

$R^{13}$ and $R^{14}$ can alternatively join to form: —(CH$_2$)$_4$—, —(CH$_2$)$_5$—, —CH$_2$CH$_2$N(R$^{15}$)CH$_2$CH$_2$— or —CH$_2$CH$_2$OCH$_2$CH$_2$—;

$R^{15}$ is: hydrogen or methyl;

each of $R^{20}$ and $R^{21}$ is independently:
   hydrogen, C$_1$-C$_6$ alkyl substituted with 0-3 R$^{11}$, C$_3$-C$_6$ alkoxyalkyl substituted with 0-3 R$^{11}$, C$_1$-C$_6$ alkylcarbonyl substituted with 0-3 R$^{11}$, C$_1$-C$_6$ alkoxycarbonyl substituted with 0-3 R$^{11}$, C$_1$-C$_6$ alkylaminocarbonyl substituted with 0-3 R$^{11}$, benzoyl substituted with 0-3 R$^{12}$, phenoxycarbonyl substituted with 0-3 R$^{12}$, phenylaminocarbonyl substituted with 0-3 R$^{12}$, or any group that, when administered to a mammalian subject as part of a compound of formula (I), cleaves to form a free hydroxyl, free amino or free sulfhydryl;

each of $R^{22}$ and $R^{23}$ is independently:
   hydrogen, C$_1$-C$_8$ alkyl substituted with 0-3 R$^{31}$, C$_2$-C$_8$ alkenyl substituted with 0-3 R$^{31}$, C$_2$-C$_8$ alkynyl substituted with 0-3 R$^{31}$, a C$_3$-C$_{14}$ carbocyclic ring system substituted with 0-5 R$^{31}$ or 0-5 R$^{32}$, or
   a 5- to 10-membered heterocyclic ring system containing 1 to 4 heteroatoms independently selected from oxygen, nitrogen or sulfur, the heterocyclic ring system being substituted with 0-2 R$^{32}$;

each $R^{31}$ is independently:
  keto, halogen, cyano, —CH$_2$N(R$^{13}$) (R$^{14}$), —N(R$^{13}$) (R$^{14}$), —C(=O)O(R$^{13}$), —C(=O) (R$^{11}$), —OC(=O) (R$^{13}$), —O(R$^{13}$), C$_2$-C$_6$ alkoxyalkyl, —S(=O)$_m$(R$^{13}$), —NHC(=NH)NH(R$^{13}$), —C(=NH)NH(R$^{13}$), —C(=O)N(R$^{13}$) (R$^{14}$), —N(R$^{14}$)C(=O) (R$^{13}$), =N—O(R$^{14}$), —N(R$^{14}$)C(=O)O(R$^{14}$), —OC(=O)N(R$^{13}$) (R$^{14}$), —N(R13)C(=O)N(R$^{13}$) (R$^{14}$), —N(R$^{14}$)S(=O)2N(R$^{13}$) (R$^{14}$), —N(R$^{14}$)S(=O)$_2$(R$^{13}$), —S(=O)$_2$N(R$^{13}$) (R$^{14}$), C$_1$-C$_4$ alkyl, C$_2$-C$_4$ alkenyl, C$_3$-C$_{10}$ cycloalkyl, C$_3$-C$_6$ cycloalkylmethyl, phenylmethyl, phenethyl, phenoxy, phenylmethoxy, nitro, C$_7$-C$_{10}$ arylalkyl, hydroxamic acid, hydrazide, oxime, boronic acid, sulfonamide, formyl, C$_3$-C$_6$ cycloalkoxy, C$_1$-C$_4$ alkyl substituted with —N (R$^{13}$) (R$^{14}$), C$_1$-C$_4$ hydroxyalkyl, methylenedioxy, ethylenedioxy, C$_1$-C$_4$ haloalkyl, C$_1$-C$_4$ haloalkoxy, C$_1$-C$_4$ alkoxycarbonyl, C$_1$-C$_4$ alkylcarbonyloxy, C$_1$-C$_4$ alkylcarbonyl, C$_1$-C$_4$ alkylcarbonylamino, —OCH$_2$C(=O)O(R$^{13}$), 2-(1-morpholino)ethoxy, azido, —C(R$^{14}$)=N—O(R$^{14}$),
  a C$_5$-C$_{14}$ carbocyclic residue substituted with 0–5 R$^{32}$,
  or a 5- to 10-membered heterocyclic ring system containing 1 to 4 heteroatoms independently selected from oxygen, nitrogen or sulfur, the heterocyclic ring system being substituted with 0–2 R$^{32}$;

each $R^{32}$ when a substituent on carbon, is independently:
  phenethyl, phenoxy, C$_3$-C$_{10}$ cycloalkyl, C$_3$-C$_6$ cycloalkylmethyl, C$_7$-C$_{10}$ arylalkyl, hydrazide, oxime, C$_2$-C$_6$ alkoxyalkyl, methylenedioxy, ethylenedioxy, C$_1$-C$_4$ alkylcarbonyloxy, —NHS(=O)$_2$(R$^{14}$), phenylmethoxy, halogen, 2-(1-morpholino)ethoxy, —C(=O)O(R$^{13}$), hydroxamic acid, —C(=O)N(R$^{13}$)N(R$^{13}$) (R$^{14}$), cyano, boronic acid, sulfonamide, formyl, C$_3$—C$_6$ cycloalkoxy, C$_1$-C$_4$ haloalkyl, C$_1$-C$_4$ haloalkoxy, C$_2$-C$_4$ haloalkenyl, C$_2$-C$_4$ haloalkynyl, —N(R$^{13}$) (R$^{14}$), —C(R$^{14}$)=N—O(R$^{14}$), —NO$_2$, —O(R$^{13}$), —N(R$^{40}$) (R$^{41}$), —S(=O)m(R$^{13}$), —S(=O)$_m$N(R$^{13}$) (R$^{14}$), —C(=O)N(R$^{13}$) (R$^{14}$), —OC(=O)N(R$^{13}$) (R$^{14}$), —C(=O) (R$^{11}$), —OC(=O) (R$^{11}$), —OC(=O)O(R$^{13}$), phenyl, —C(=O)N(R$^{13}$)—(C$_1$-C$_4$ alkyl) N(R$^{13}$) (R$^{14}$), —C(=O)N(R$^{40}$) (R$^{41}$), —C(=O)—(C$_1$-C$_4$ alkyl)—N(R$^{13}$)C(=O)O(R$^{13}$),
  C$_1$-C$_4$ alkoxy substituted with 0–4 groups selected from:
    R$^{11}$, C$_3$-C$_6$ cycloalkyl, —C(=O)O(R$^{13}$), —C(=O)N(R$^{13}$) (R$^{14}$), —N(R$^{13}$) (R$^{14}$) or hydroxyl,
  C$_1$-C$_4$ alkyl substituted with 0–4 groups selected from:
    R$^{11}$, =N(R$^{14}$), =NN(R$^{13}$)C(=O)N(R$^{13}$) (R$^{14}$) or —N (R$^{13}$) (R$^{14}$),
  C$_2$-C$_4$ alkenyl substituted with 0–4 R$^{11}$,
  C$_2$-C$_4$ alkynyl substituted with 0–4 R$^{11}$,
  a 5- or 6-membered heterocyclic ring containing from 1 to 4 heteroatoms independently selected from oxygen, nitrogen or sulfur,
  a 3- or 4-carbon chain attached to an adjacent carbon on the ring to which it is appended, to form a fused 5- or 6-membered ring, said 5- or 6-membered ring being optionally substituted on the aliphatic carbons with halogen, C$_1$-C$_4$ alkyl, C$_1$-C$_4$ alkoxy, hydroxyl, —N (R$^{13}$) (R$^{14}$), or
  when R$^{32}$ is attached to a saturated carbon atom, R$^{32}$ may be =O or =S;

each $R^{32}$ when a substituent on nitrogen, is independently:
  phenyl, phenylmethyl, phenethyl, hydroxyl, C$_1$-C$_4$ hydroxyalkyl, C$_1$-C$_4$ alkoxy, C$_1$-C$_4$ alkyl, C$_3$-C$_6$ cycloalkyl, C$_3$-C$_6$ cycloalkylmethyl, —CH$_2$N(R$^{13}$) (R$^{14}$), —N (R$^{13}$) (R$^{14}$), C$_2$-C$_6$ alkoxyalkyl, C$_1$-C$_4$ haloalkyl, C$_1$-C$_4$ alkoxycarbonyl, —C(=O) OH, C$_1$-C$_4$ alkylcarbonyloxy, C$_1$-C$_4$ alkylcarbonyl or —C(R$^{14}$)=N—O(R$^{14}$);

$R^{40}$ is: hydrogen or C$_1$-C$_3$ alkyl; and, $R^{41}$ is: —C(=O)N(R$^{13}$) (R$^{14}$), —C(=O)N(R$^{13}$)NH(R$^{14}$), —C(=O)C(R$^{11}$)$_2$N(R$^{13}$) (R$^{14}$), —C(=O)C(R$^{11}$)2N(R$^{13}$)NH(R$^{14}$), —C(=O)C(R$^{11}$)$_2$N(R$^{13}$)C(=O)O(R$^{13}$), —C(=O) H, —C(=O) (R$^{11}$), —C(=O)—(C$_1$-C$_4$ alkyl)—N(R$^{13}$) (R$^{14}$), —C(=O)—(C$_1$-C$_4$ alkyl)—N(R$^{13}$)C(=O)O(R$^{13}$) or 1–3 amino acids linked together via amide bonds and linked to the N atom via the carboxylate terminus;

provided that:
  R$^4$, R$^{4A}$, R$^7$ and R$^{7A}$ are not all hydrogen; when R$^4$ and R$^{4A}$ are both hydrogen, R$^{22}$ is not hydrogen, and when R$^7$ and R$^{7A}$ are both hydrogen, R$^{23}$ is not hydrogen.

2. A compound of claim 1, or a pharmaceutically acceptable salt or prodrug form thereof wherein:

Each of R$^4$ and R$^7$ is independently:
  hydrogen or C$_1$-C$_3$ alkyl substituted with 0–1 R$^{11}$;

Both R$^{4A}$ and R$^{7A}$ are hydrogen;

R$^5$ is —O(R$^{20}$);

R$^{5A}$ is hydrogen;

R$^6$ is hydrogen or —O(R$^{21}$);

R$^{6A}$ is hydrogen;

R$^8$ is hydrogen;

R$^{11}$ is:
  hydrogen, halogen, —O(R$^{13}$), C$_3$-C$_{10}$ cycloalkyl, C$_1$-C$_4$ alkyl, aryl(C$_1$-C$_3$ alkyl) substituted with 0–2 R$^{12}$; aryl substituted with 0–2 R$^{12}$, or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl or oxazolidinyl, where the heterocyclic ring system is substituted with 0–3 R$^{12}$;

Each R$^{12}$, when a substituent on carbon, is independently:
  phenylmethoxy, halogen, methyl, C$_1$-C$_4$ alkoxy, trifluoromethyl, 2-(1-morpholino)ethoxy, —C(=O)OH, hydroxamic acid, hydrazide, —C(R$^{14}$)=N—O(R$^{14}$), cyano, boronic acid, sulfonamide, formyl, C$_3$-C$_6$ cycloalkoxy, C$_1$-C$_4$ alkyl substituted with —N(R$^{13}$) (R$^{14}$), —N(R$^{13}$) (R$^{14}$), hydroxy or hydroxymethyl;

Each R$^{12}$, when a substituent on nitrogen, is methyl;

R$^{13}$ is: hydrogen, C$_1$-C$_4$ alkyl, C$_2$-C$_4$ alkenyl or phenylmethyl;

Each R$^{14}$ is independently:
  hydrogen, hydroxy, trifluoromethyl, C$_1$-C$_4$ alkyl, C$_1$-C$_4$ alkoxy, C$_2$-C$_4$ alkenyl, phenylmethyl or amino;

Each of R$^{20}$ and R$^{21}$ is independently:
  hydrogen or any group that, when administered to a mammalian subject as part of a compound of formula (I), cleaves to form a free hydroxyl;

Each of R$^{22}$ and R$^{23}$ is independently:
  hydrogen, C$_1$-C$_8$ alkyl substituted with 0–3 R$^{31}$, C$_2$-C$_6$ alkenyl substituted with 0–3 R$^{31}$, or C$_2$-C$_4$ alkynyl substituted with 0–3 R31;

Z is: O or N ($R^{24A}$);

$R^{24A}$ is: hydrogen or $C_1$-$C_6$ alkyl;

Each of $R^{25}$ and $R^{27}$ is independently:
  hydrogen, $C_1$-$C_4$ alkyl substituted with 0–3 $R^{31}$, or $C_3$-$C_4$ alkenyl substituted with 0–3 $R^{31}$;

Each of $R^{26}$ and $R^{28}$ is independently:
  hydrogen or halogen;

Each $R^{31}$ is independently:
  halogen, —O($R^{13}$), $C_1$-$C_4$ alkyl, $C_3$-$C_{10}$ cycloalkyl, —S(=O)$_m$($R^{13}$), —C($R^{14}$)=N—O($R^{14}$), —C(=O)O($R^{13}$), aryl substituted with 0–5 $R^{32}$, or a heterocyclic ring system selected from pyridyl, indazolyl, pyrimidinyl, triazinyl, furanyl, thienyl, pyrrolyl, pyrazolyl, imidazolyl, tetrazolyl, benzofuranyl, indolyl, quinolinyl, isoquinolinyl or oxazolidinyl, where the heterocyclic ring system is substituted with 0–2 $R^{32}$;

Each $R^{32}$, when a substituent on carbon, is independently:
  phenylmethoxy, halogen, 2-(1-morpholino)ethoxy, —C(=O)O($R^{13}$), hydroxamic acid, —C(=O)N($R^{13}$)N($R^{13}$) ($R^{14}$), cyano, boronic acid, sulfonamide, formyl, $C_3$-$C_6$ cycloalkoxy, —N($R^{13}$)($R^{14}$), —C($R^{14}$)=N—O($R^{14}$), —NO$_2$, —O($R^{13}$), —N($R^{40}$) ($R^{41}$), —S(=O)$_m$($R^{13}$), —S(=O)$_m$N($R^{13}$)($R^{14}$), —C(=O)N($R^{13}$) ($R^{14}$), —OC(=O)N($R^{13}$)($R^{14}$), —C(=O) ($R^{11}$), —OC(=O) ($R^{11}$), —OC(=O)O($R^{13}$), phenyl, —C(=O)N($R_{13}$)—($C_1$-$C_4$ alkyl) —N($R^{13}$) ($R^{14}$), —C(=O)N($R^{40}$) ($R^{41}$), $C_1$-$C_4$ haloalkyl, $C_1$-$C_4$ haloalkoxy, $C_2$-$C_4$ haloalkenyl, $C_2$-$C_4$ haloalkynyl, —C(=O)C($R^{11}$)$_2$N($R^{13}$)($R^{14}$), —C(=O)C($R^{11}$)$_2$N($R^{13}$)NH($R^{14}$), —C(=O)C($R^{11}$)$_2$N($R^{13}$)C(=O)O($R^{13}$), —C(=O)—($C_1$-$C_4$ alkyl)—N($R^{13}$) ($R^{14}$), —C(=O)—($C_1$-$C_4$ alkyl)—N($R^{13}$)C(=O)O($R^{13}$), $C_1$-$C_4$ alkoxy substituted with 0–3 groups selected from $R^{11}$, $C_3$-$C_6$ cycloalkyl, —C(=O)N($R^{13}$) ($R^{14}$), —N($R^{13}$) ($R^{14}$) or hydroxyl,
  $C_1$-$C_4$ alkyl substituted with 0–3 groups selected from $R^{11}$, =N($R^{14}$), =NN($R^{13}$)C(=O)N($R^{13}$) ($R^{14}$) or —N($R^{13}$) ($R^{14}$),
  $C_2$-$C_4$ alkenyl substituted with 0–3 $R^{11}$,
  $C_2$-$C_4$ alkynyl substituted with 0–3 $R^{11}$, or
  a 5- or 6-membered heterocyclic ring containing from 1 to 4 heteroatoms independently selected from oxygen, nitrogen or sulfur; and Each $R^{32}$ when a substituent on nitrogen, is methyl.

3. A compound of claim 1, or a pharmaceutically acceptable salt or prodrug form thereof wherein:

Both $R^4$ and $R^7$ are phenylmethyl;

Both $R^{4A}$ and $R^{7A}$ are hydrogen;

$R^6$ is hydroxy;

$R^{6A}$ is hydrogen;

$R^8$ is hydrogen;

T is —N($R^{22}$)P(=O)N($R^{23}$)—;

Each of $R^{22}$ and $R^{23}$ is independently:
  hydrogen, allyl, methyl, ethyl, propyl, cyclopropylmethyl, n-butyl, i-butyl, pyridinylmethyl, indazolylmethyl, aminoindazolylmethyl, carbomethoxy-indazolylmethyl, chloroindazolylmethyl, fluoroindazolylmethyl, methylindazolylmethyl, ethylamino-indazolylmethyl, methallyl, n-pentyl, i-pentyl, hexyl, phenylmethyl, isoprenyl, propargyl, methoxyethyl, cyclohexylmethyl, dimethylbutyl, ethoxyethyl, naphthylmethyl, methyloxazolinylmethyl, vinyloxyethyl, pentafluorophenylmethyl, quinolinylmethyl, carboxybenzyl, chloro-thienyl, benzyloxyphenylmethyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2$NC(=O))-benzyl, carbomethoxybenzyl, carboethoxybenzyl, tetrazolylbenzyl, dimethylallyl including —CH$_2$CH=C(CH$_3$)$_2$, aminomethylbenzyl, (O—benzylformaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl)ethylbenzyl, (CH$_3$C(=NOH))-benzyl, ($H_2$NNHC(=O))-benzyl, ($H_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_{2O}$)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, (CH$_3$CH$_2$NHC(=O))-benzyl, N,N-diethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl—C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)-benzyl, ($H_2$NSO$_2$)-benzyl, dihydroxyethylbenzyl, (MeHNC(=O)NH)-benzyl, ($H_2$NC(=O)NH)-benzyl, (HC(=O)NH)benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C—C(=O))benzyl, (N-methyl- N-ethylaminoethyl)aminocarbonylbenzyl, (pyrrolidinylethyl)aminocarbonylbenzyl or (piperidinylethyl)aminocarbonylbenzyl;

Z is: O; and n is: 0.

4. A compound of claim 1, or a pharmaceutically acceptable salt or prodrug form thereof wherein:

Both $R^4$ and $R^7$ are phenylmethyl;
Both $R^{4A}$ and $R^{7A}$ are hydrogen;
$R^6$ is hydroxy;
$R^{6A}$ is hydrogen;
$R^8$ is hydrogen;
T is $-N(R^{22})P(=O)N(R^{23})-$; and
Both $R^{22}$ and $R^{23}$ are: cyclopropylmethyl, n-butyl, 2-naphthalenylmethyl, phenylmethyl, 4-(hydroxymethyl)phenylmethyl, 3-(methylamino)phenylmethyl, 4-(hydroxy)phenylmethyl or 3-(hydroxymethyl)phenylmethyl);

Z is: O; and n is: 0.

* * * * *